(12) United States Patent
Henrich et al.

(10) Patent No.: US 9,937,217 B2
(45) Date of Patent: Apr. 10, 2018

(54) METHOD OF INHIBITING ABCG2 AND RELATED TREATMENTS

(71) Applicant: The United States of America, as represented by the Secretary, Department of Health and Human Services, Washington, DC (US)

(72) Inventors: Curtis J. Henrich, Rockville, MD (US); Heidi R. Bokesch, Frederick, MD (US); Susan E. Bates, Bethesda, MD (US); Robert W. Robey, Laurel, MD (US); Suneet Shukla, Rockville, MD (US); Suresh V. Ambudkar, Gaithersburg, MD (US); Michael C. Dean, Frederick, MD (US); James B. McMahon, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 7 days.

(21) Appl. No.: 14/822,437

(22) Filed: Aug. 10, 2015

(65) Prior Publication Data
US 2015/0342978 A1 Dec. 3, 2015

Related U.S. Application Data

(62) Division of application No. 12/742,039, filed as application No. PCT/US2008/082414 on Nov. 5, 2008, now Pat. No. 9,114,102.

(60) Provisional application No. 60/986,155, filed on Nov. 7, 2007.

(51) Int. Cl.
| | |
|---|---|
| A61K 31/7028 | (2006.01) |
| A61K 31/196 | (2006.01) |
| A61K 31/4741 | (2006.01) |
| A61K 31/4985 | (2006.01) |
| A61K 36/06 | (2006.01) |
| A61K 31/015 | (2006.01) |
| A61K 31/28 | (2006.01) |
| A61K 31/4155 | (2006.01) |
| A61K 31/439 | (2006.01) |
| A61K 31/4439 | (2006.01) |
| A61K 31/48 | (2006.01) |
| A61K 31/505 | (2006.01) |
| A61K 31/655 | (2006.01) |
| A61K 31/7048 | (2006.01) |

(52) U.S. Cl.
CPC .......... *A61K 36/06* (2013.01); *A61K 31/015* (2013.01); *A61K 31/28* (2013.01); *A61K 31/4155* (2013.01); *A61K 31/439* (2013.01); *A61K 31/4439* (2013.01); *A61K 31/4741* (2013.01); *A61K 31/48* (2013.01); *A61K 31/505* (2013.01); *A61K 31/655* (2013.01); *A61K 31/7048* (2013.01)

(58) Field of Classification Search
CPC .. A61K 31/015; A61K 31/28; A61K 31/4155; A61K 31/439; A61K 31/4439; A61K 36/06; A61K 31/48; A61K 31/505; A61K 31/655; A61K 31/7048; A61K 31/4741
USPC .......... 514/26, 25, 284, 183, 179; 536/5, 4.1, 536/6.4
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |

FOREIGN PATENT DOCUMENTS

| | | | |
|---|---|---|---|
| EP | 1 864 972 A1 | 12/2007 | |
| WO | WO 02/053138 A2 | 7/2002 | |
| WO | WO 2006/031614 A2 | 3/2006 | |
| WO | WO 2006031614 A2 * | 3/2006 | ........... A61K 31/535 |
| WO | WO 2008/039254 A2 | 4/2008 | |
| WO | WO 2008/062466 A2 | 5/2008 | |
| WO | WO 2009/088831 A2 | 7/2009 | |

OTHER PUBLICATIONS

Burg et al. (Mol. Pharmacol, vol. 62, No. 5, 1160-1166, 2002).*
Gura, Trisha; Sience, vol. 278, Nov. 7, 1997.*
Jekunen et al. (Biochemical Pharmacology (1993), 45(10), 2079-85) (abstract sent).*
Nicol et al. ( Brazilian Journal of Medical and Biological Research (2002) 35: 549-553).*
Abbott et al., "Low levels of ABCG2 expression in adult AML blast samples," *Blood*, 100 (13), 4594-4601 (2002).
Ahmed-Belkacem et al., "Inhibitors of cancer cell multidrug resistance mediated by breast cancer resistance protein (BCRP/ABCG2)," *Anti-cancer Drugs*, 17 (3), 239-243-(2006).
Ahmed-Belkacem et al., "Flavonoid structure-activity studies identify 6-prenylchrysin and tectochrysin as potent and specific inhibitors of breast cancer resistance protein ABCG2,"*Cancer Res.*, 65 (11), 4852-4860 (2005).
Allen et al., "Potent and specific inhibition of the breast cancer resistance protein multidrug transporter in vitro and in mouse intestine by a novel analogue of fumitremorgin C," *Mol. Cancer Ther.*, 1 (6), 417-425 (2002).

(Continued)

*Primary Examiner* — Shaojia Anna Jiang
*Assistant Examiner* — Michael C Henry
(74) *Attorney, Agent, or Firm* — Leydig, Voit & Mayer, Ltd.

(57) ABSTRACT

Disclosed are methods of enhancing the chemotherapeutic treatment of tumor cells, reducing resistance of a cancer cell to a chemotherapeutic agent, a method of inhibiting ABCG2 or MRP1 in a mammal afflicted with cancer, and a method of increasing the bioavailability of an ABCG2 substrate drug in a mammal. The methods comprise administering peliomycin and other compounds described herein.

9 Claims, 7 Drawing Sheets

(56) References Cited

OTHER PUBLICATIONS

Alvarez et al., "Using the national cancer institute anticancer drug screen to assess the effect of MRP expression on drug sensitivity profiles," *Mol. Pharmacol.*, 54, 802-814 (1998).

Benderra et al., "MRP3, BCRP, and P-glycoprotein activities are prognostic factors in adult acute myeloid leukemia," *Clin. Cancer Res.*, 11 (21), 7764-7772 (2005).

Boumendjel et al., "Anticancer multidrug resistance mediated by MRP1: recent advances in the discovery of reversal agents," *Med. Res. Rev.*, 25 (4), 453-472 (2005).

Breedveld et al., "The effect of Bcrp1 (Abcg2) on the in vivo pharmacokinetics and brain penetration of imatinib mesylate (Gleevec): implications for the use of breast cancer resistance protein and P-glycoprotein inhibitors to enable the brain penetration of imatinib in patients," *Cancer Res.*, 65 (7), 2577-2582 (2005).

Choi et al., "Curcumin down-regulates the multidrug-resistance mdr1 b gene by inhibiting the P13K/Akt/NF kappa B pathway," *Cancer Letters*, 259 (1), 111-118 (2008).

Damiani et al., "The prognostic value of P-glycoprotein (ABCB) and breast cancer resistance protein (ABCG2) in adults with de novo acute myeloid leukemia with normal karyotype," *Haematologica*, 91 (6), 825-828 (2006).

Dean et al., "Tumour stem cells and drug resistance," *Nat. Rev. Cancer.*, 5, 275-284 (2005).

Diestra et al., "Frequent expression of the multi-drug resistance-associated protein BCRP/MXR/ABCP/ABCG2 in human tumours detected by the BXP-21 monoclonal antibody in paraffin-embedded material," *J. Pathol.*, 198, 213-219 (2002).

Durr, "Biologic and biochemical effects of mitoxantrone," *Semin. Oncol.*, 11 (3 Suppl 1), 3-10 (1984) Abstract.

Gura, "Systems for identifying new drugs are often faulty," *Science*, 278, 1041-1042, (1997).

Henrich et al., "A high-throughput cell-based assay for inhibitors of ABCG2 activity," *J. Biomol. Screen.*, 11 (2), 176-183 (2006).

Henrich et al., "New inhibitors of ABCG2 identified by high-throughput screening," *Mol. Cancer Ther.*, 6 (12), 3271-3278 (2007).

Holbeck, "Update on NCI in vitro drug screen utilities," *Eur. J. Cancer*, 40, 785-793 (2004).

Horenstein et al., "Synthesis of unprotected (.×-.)-tunichrome An-1, a tunicate blood pigment," *J. Am. Chem. Soc.*, 111, 6242-6246 (1989).

Ikeda et al., "*Aspergillus* species strain M39 produces two naphtho-gamma-pyrones that reverse drug resistance in human KB cells," *Int. J. Cancer*, 45, 508-513 (1990).

Ikeda, "*Aspergillus* species strain M39 produces two naphtho-gamma-pyrones that reverse drug resistance in human KB cells," *Med. J. Kagoshima Univ.*, 42 (4), 367-377 (1991).

Jonker et al., "Role of breast cancer resistance protein in the bioavailability and fetal penetration of topotecan," *J. Natl. Cancer Inst.*, 92 (20), 1651-1656 (2000).

Jonker et al., "The breast cancer resistance protein protects against a major chlorophyll-derived dietary phototoxin and protoporphyria," *Proc. Natl. Acad. Sci. USA*, 99 (24), 15649-15654 (2002).

Kamath et al., "Overexpression of P-glycoprotein and alterations in topoisomerase II in P388 mouse leukemia cells selected in vivo for resistance to mitoxantrone," *Biochem. Pharmacol.*, 44, 937-945 (1992).

Kim et al., "Synthesis of tunichromes Mm-1 and Mm-2, blood pigments of the iron-assimilating tunicate, *molgula manhattensis*," *Tetrahedron Letters*, 31 (49), 7119-7122 (1990).

Krishnamurthy et al., "Role of ABCG2/BCRP in biology and medicine," *Annu. Rev. Pharmacol. Toxicol.*, 46, 381-410 (2006).

Kruijtzer et al., "Increased oral bioavailability of topotecan in combination with the breast cancer resistance protein and P-glycoprotein inhibitor GF120918," *J. Clin. Oncol.*, 20 (13), 2943-2950 (2002).

Marchand et al., "Peptide alkaloids. VII. Lasiodines A and B, alkaloids of Lasiodiscus marmoratus C. H. Wright (Rhamnaceae)," *Tetrahedron*, 25, 937-954 (1969).

McDonald et al., "Botryllamides A-D,new brominated tyrosine derivatives from styelid ascidians of the genus *Botryllus*," *Tetrahedron*, 51 (18), 5237-5244 (1995).

Nagashima et al., "BCRP/ABCG2 levels account for the resistance to topoisomerase I inhibitors and reversal effects by gefitinib in non-small cell lung cancer," *Cancer Chemother Pharmacol.*, 58, 594-600 (2006).

Oltz et al., "The tunichromes. A class of reducing blood pigments from sea squirts: isolation, structures, and vanadium chemistry," *J. Am. Chem. Soc.*, 110, 6162-6172 (1988).

Özvegy-Laczka et al., "Function-dependent conformational changes of the ABCG2 multidrug transporter modify its interaction with a monoclonal antibody on the cell surface," *J. Biol. Chem.*, 280 (6), 4219-4227 (2005).

Phuwapraisirisan et al., "Phenylethyl cinnamides: a new series of alpha-glucosidase inhibitors from the leaves of Aegle marmelos," *Bioorg. Med. Chem. Lett.*, 18, 4956-4958 (2008).

Plasschaert et al., "Breast cancer resistance protein (BCRP) in acute leukemia," *Leukemia and Lymphoma*, 45 (4), 649-654 (2004).

Price et al., "Peliomycin, A New Cytotoxic Agent. II. Biological Properties," *Antimicrobial Agents and Chemotherapy*, 161, 95-99 (1963).

Rabindran et al., "Reversal of a novel multidrug resistance mechanism in human colon carcinoma cells by fumitremorgin C," *Cancer Res.*, 58, 5850-5858 (1998).

Rao et al., "Botryllamides E-H, four new tyrosine derivatives from the ascidian Botrylloides tyreum," *J. Nat. Prod.*, 67, 1064-1066 (2004).

Robey et al., "A functional assay for detection of the mitoxantrone resistance protein, MXR (ABCG2)," *Biochim. Biophys. Acta*, 1512, 171-182 (2001).

Robey et al., "Mutations at amino-acid 482 in the ABCG2 gene affect substrate and antagonist specificity," *Br. J. Cancer*, 89, 1971-1978 (2003).

Robey et al., "ABCG2: determining its relevance in clinical drug resistance," *Cancer Metastasis Rev.*, 26, 39-57 (2007).

Robey et al., "Pheophorbide a is a specific probe for ABCG2 function and inhibition," *Cancer Res.*, 64, 1242-1246 (2004).

Robey et al., "Overexpression of the Atp-binding cassette half-transporter, ABCG2 (Mxr/BCrp/ABCP1), in flavopiridol-resistant human breast cancer cells," *Clin. Cancer Res.*, 7, 145-152 (2001).

Sakurai et al., "TMC-256A1 and C1, new inhibitors of IL-4 signal transduction produced by Aspergillus niger var niger Tc 1629," *J. Antibio.*, 55 (8), 685-692 (2002).

Sarkadi et al., "Human multidrug resistance ABCB and ABCG transporters: participation in a chemoimmunity defense system," *Physiol. Rev.*, 86, 1179-1236 (2006).

Schnier et al., Identification of cytosolic aldehyde dehydrogenase 1 from non-small cell lung carcinomas as a flavopiridol-binding protein, *FEBS Letters*, 454, 100-104 (1999).

Scudiero et al., "Evaluation of a soluble tetrazolium/formazan assay for cell growth and drug sensitivity in culture using human and other tumor cell lines," *Cancer Res.*, 48, 4827-33 (1988).

Shoemaker, "The NCI60 human tumour cell line anticancer drug screen," *Nat. Rev. Cancer*, 6 (10), 813-823 (2006).

Shukla et al., "The calcium channel blockers, 1,4-dihydropyridines, are substrates of the multidrug resistance-linked ABC drug transporter, ABCG2," *Biochemistry*, 45 (29), 8940-8951 (2006).

Skehan et al., "New colorimetric cytotoxicity assay for anticancer-drug screening," *J. Natl. Cancer Inst.*, 82 (13), 1107-1112 (1990).

Stewart et al., "Gefitinib enhances the antitumor activity and oral bioavailability of irinotecan in mice," *Cancer Res.*, 64, 7491-7499 (2004).

Stonard et al., "Linear peptide alkaloids from the sponge *Cliona celata* (Grant). Celenamides C and D," *Canada J. Chem.*, 58 (20), 2121-2126 (1980).

Suzuki et al., "ABCG2 transports sulfated conjugates of steroids and xenobiotics," *J. Biol. Chem.*, 278, 22644-22649 (2003).

Szakács et al., "Targeting multidrug resistance in cancer," *Nat. Rev. Drug Dis.*, 5 (3), 219-234 (2006).

(56) References Cited

OTHER PUBLICATIONS

Szoka et al., "Comparative properties and methods of preparation of lipid vesicles (liposomes)," *Ann. Rev. Biophys. Bioeng.*, 9, 467-508 (1980).
Takano et al., "Expression and function of efflux drug transporters in the intestine," *Pharmacol. Ther.*, 109, 137-161 (2006).
Turner et al., "ABCG2 expression, function, and promoter methylation in human multiple myeloma," *Blood*, 108(12), 3881-3889 (2006).
Uggla et al., "BCRP mRNA expression v. clinical outcome in 40 adult AML patients," *Leuk. Res.*, 29 (2), 141-146 (2005).
Wasserman et al., "Clinical comparison of the nitrosoureas," *Cancer*, 36, 1258-1268 (1975).
Wilson et al., "Gene expression profiling of adult acute myeloid leukemia identifies novel biologic clusters for risk classification and outcome prediction," *Blood*, 108, 685-696 (2006).
Xu et al., "Human multidrug transporter ABCG2, a target for sensitizing drug resistance in cancer chemotherapy," *Curr. Med. Chem.*, 14, 689-701 (2007).
Yoh et al., "Breast cancer resistance protein impacts clinical outcome in platinum-based chemotherapy for advanced non-small cell lung cancer," *Clin. Cancer Res.*, 10, 1691-1697 (2004).
Zhang et al., "Nigerasperones A approximately C, new monomeric and dimeric naphtho-gamma-pyrones from a marine alga-derived endophytic fungus *Aspergillus niger* EN-13," *J. Antibia*, 60 (3), 204-210 (2007).
Zhang et al., "Flavonoids are inhibitors of breast cancer resistance protein (ABCG2)-mediated transport," *Mol. Pharmacol.*, 65 (5), 1208-1216 (2004).
Zee Cheng et al., "Preparation and antileukemic activity of some alkoxybenzo(c)phenanthridinium salts and corresponding dihydro derivatives" *J. Med. Chem.*, 18(1), 66 71 (1975).
International Search Report, Application No. PCT/US2008/082414, dated Oct. 12, 2009.
International Preliminary Report on Patentability, Application No. PCT/US2008/082414, dated May 20, 2010.
Written Opinion of the International Searching Authority, Application No. PCT/US2008/082414, dated May 20, 2010.
Office Action, U.S. Appl. No. 12/742,039, dated Aug. 31, 2012.
Office Action, U.S. Appl. No. 12/742,039, dated Feb. 12, 2013.
Office Action, U.S. Appl. No. 12/742,039, dated Sep. 10, 2013.
Office Action, U.S. Appl. No. 12/742,039, dated Dec. 5, 2013.
Office Action, U.S. Appl. No. 12/742,039, dated Jun. 24, 2014.
Office Action, U.S. Appl. No. 12/742,039, dated Jan. 6, 2015.

\* cited by examiner

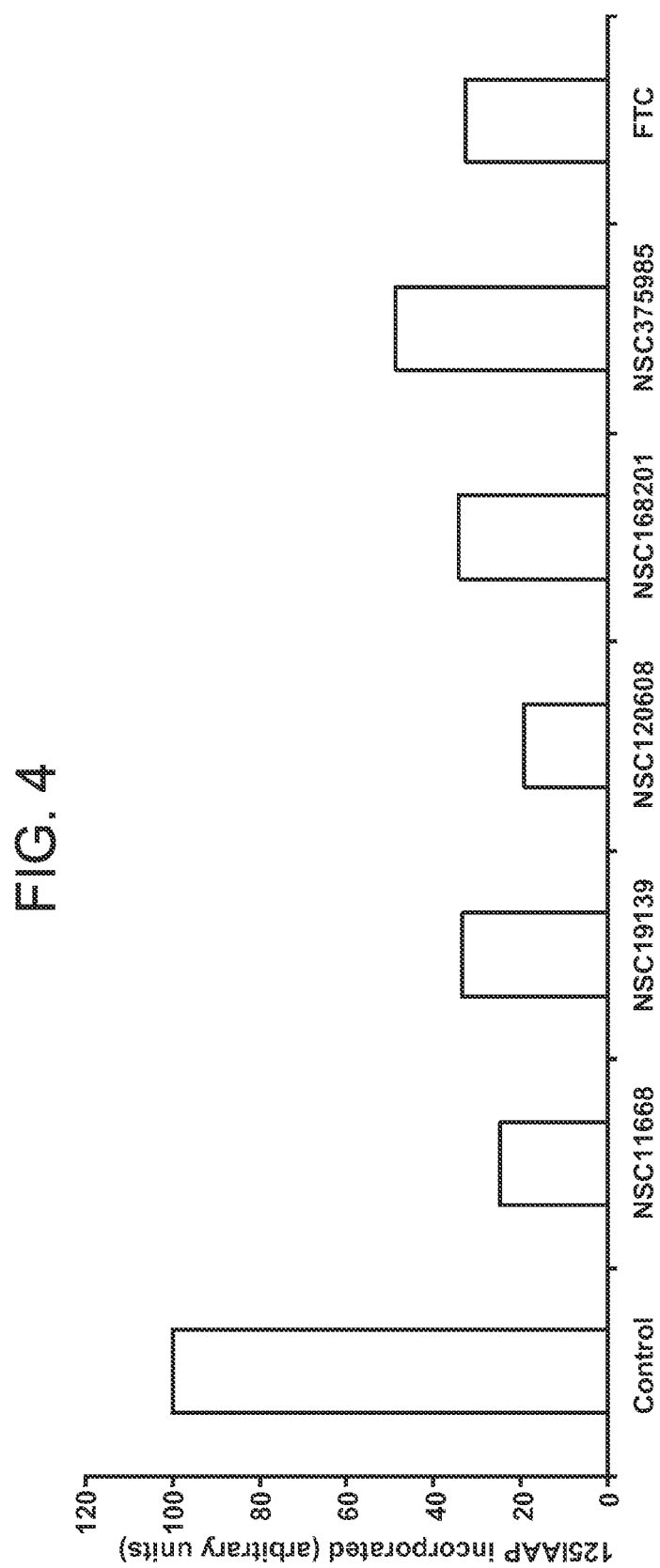

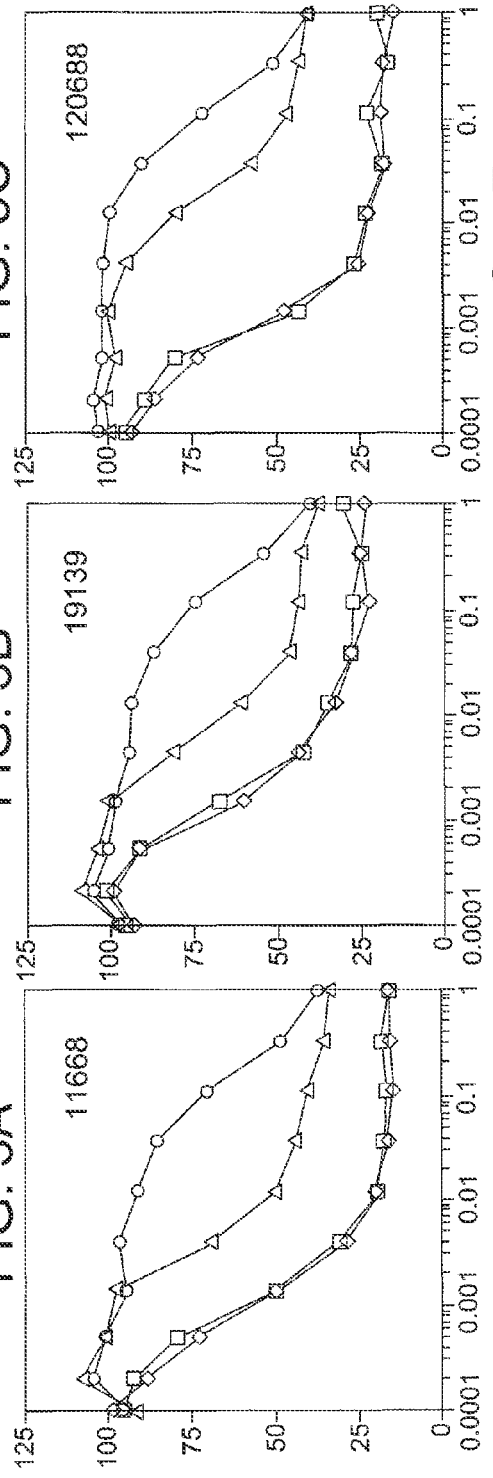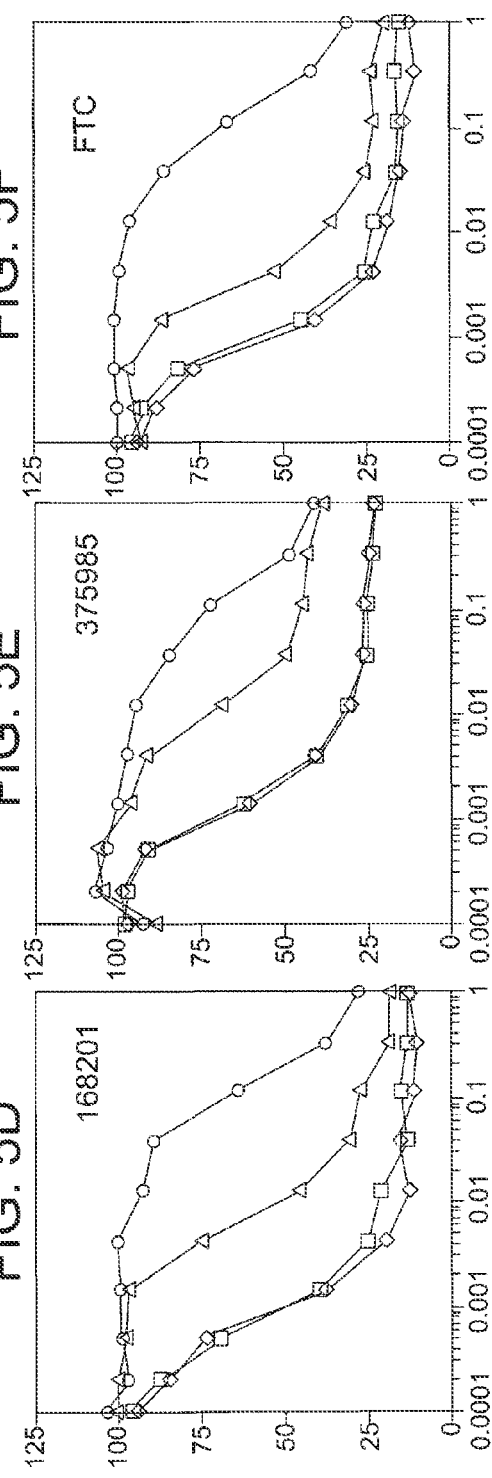

METHOD OF INHIBITING ABCG2 AND RELATED TREATMENTS

CROSS-REFERENCE TO RELATED APPLICATIONS

This patent application is a divisional of copending U.S. patent application Ser. No. 12/742,036, filed Jun. 23, 2010, which is a U.S. National Phase of International Patent Application No. PCT/US2008/082414, filed Nov. 5, 2008, which claims the benefit of U.S. Provisional Patent Application No. 60/986,155, filed Nov. 7, 2007, all of which are incorporated by reference.

BACKGROUND OF THE INVENTION

Multidrug resistance has long been recognized as a major obstacle to successful cancer chemotherapy. The multidrug resistance transporter ABCG2 (or Breast Cancer Resistance Protein 1, BCRP1), a member of the ABC (ATP-binding cassette) family of membrane transport proteins, is believed to form a part of the maternal-fetal barrier, the blood-brain barrier, and is known to limit oral absorption of some drugs (Robey et al., Cancer Metastasis Rev., 26: 39-57 (2007)). The normal physiologic functions of ABCG2 may be related to transport of a variety of natural substances to prevent intracellular accumulation of toxic compounds. ABCG2 is also an important mediator of resistance to a variety of anti-cancer drugs, including mitoxantrone, topotecan, irinotecan, flavopiridol, and methotrexate (Sarkadi et al., Physiol. Rev., 86: 1179-1236 (2006); Krishnamurthy et al., Annu. Rev. Pharmacol. Toxicol., 46: 381-410 (2006); Szakacs et al., Nat. Rev. Drug Discov., 5: 219-34 (2006); and Xu et al., Curr. Med. Chem., 14: 689-701 (2007)). Thus, inhibitors of ABCG2 activity could have important oncologic and pharmacologic applications.

Unfortunately, few, if any, clinically useful inhibitors of ABCG2 activity have been reported. Thus, there exists a desire for compounds that can inhibit ABCG2 and in turn, increase the efficacy of adjuvant chemotherapy.

BRIEF SUMMARY OF THE INVENTION

The invention provides a method of enhancing the chemotherapeutic treatment of tumor cells in a mammal with a chemotherapeutic agent, which method comprises administering to the mammal an effective amount of the chemotherapeutic agent in conjunction with an effective amount of a compound described herein that inhibits ABCG2 protein.

In an embodiment, the invention provides a method of reducing resistance of a cancer cell to a chemotherapeutic agent by inhibiting ABCG2 in a mammal, which method comprises administering to the mammal an effective amount of a compound described herein.

The invention further provides a method of inhibiting ABCG2 and/or MRP1 in a mammal afflicted with cancer, which method comprises administering to the mammal an effective amount of a compound described herein.

The invention also provides a method of increasing the bioavailability of an ABCG2 substrate drug in a mammal, which method comprises administering to the mammal an effective amount of the ABCG2 substrate drug in conjunction with an effective amount of a compound described herein that inhibits ABCG2 protein.

The invention further provides use of an ABCG2 inhibitor or an MRP1 inhibitor in the preparation of a medicament for enhancing the chemotherapeutic treatment of a mammal afflicted with cancer. The invention also provides use of an ABCG2 inhibitor or an MRP1 inhibitor in combination with a chemotherapeutic agent for treating cancer.

BRIEF DESCRIPTION OF THE SEVERAL VIEWS OF THE DRAWINGS

FIG. 4 depicts the amount of $[^{125}I]$-IAAP incorporated (average of three independent experiments) into ABCG2 (Y-axis) in the absence (control) or presence of 20 μM of the indicated compound (X-axis).

FIGS. 5A-5F depict the effect of ABCG2 inhibitor on control and ABCG2 transfected cells when treated with varying concentrations of chemotherapeutic drug SN-38, which is 7-ethyl-10-hydroxycamptothecin. The Y-axis represents the optical density of cell suspension (arbitrary units) and the X-axis represents the concentration of the chemotherapeutic drug, SN-38. Squares and diamonds represent positive control HEK 293 cells, with squares representing experiments without the ABCG2 inhibitor and the diamonds representing experiments with the ABCG2 inhibitor. Triangles and circles represent HEK 293 cells transfected with ABCG2, with triangles representing experiments conducted with the ABCG2 inhibitor, and the circles representing experiments without the ABCG2 inhibitor.

FIG. 5A depicts the effect where the ABCG2 inhibitor is NSC 11668. FIG. 5B depicts the effect where the ABCG2 inhibitor is NSC 19139. FIG. 5C depicts the effect where the ABCG2 inhibitor is NSC 120688. FIG. 5D depicts the effect where the ABCG2 inhibitor is NSC 168201. FIG. 5E depicts the effect where the ABCG2 inhibitor is 375985. FIG. 5F depicts the effect where the ABCG2 inhibitor is FTC (fumitremorgin C).

DETAILED DESCRIPTION OF THE INVENTION

Figure 1:
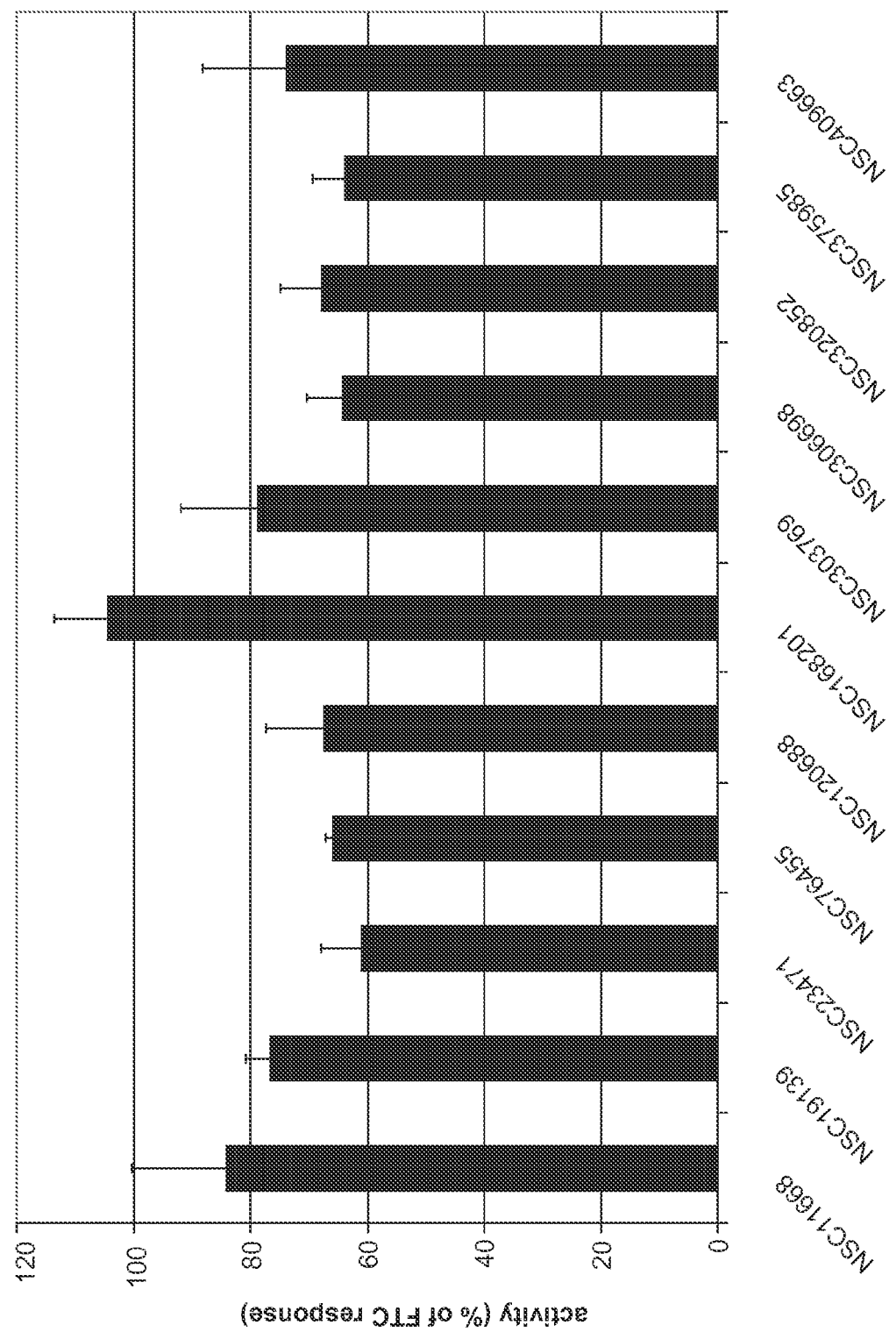
FIG. 1 depicts the activity of compounds in a pheophorbide a (PhA) screening assay in an embodiment of the invention. The compounds are assayed for their ability to cause ABCG2-overexpressing cells (NCI-H460/MX20 cells) to accumulate PhA. Each compound is tested at 10 μM (final concentration—bars) and, after resupply, in a dose-response format. Activity for each compound is normalized to the response of 10 μM FTC control wells on the same plate. Error bars represent sem (n=7-9). $IC_{50}$ values are averages of duplicate determinations for each dose.

The invention provides, in accordance with an embodiment, a method of enhancing the chemotherapeutic treatment of tumor cells in a mammal with a chemotherapeutic agent, which method comprises administering to the mammal an effective amount of the chemotherapeutic agent in conjunction with an effective amount of a compound to inhibit ABCG2 protein, said compound being selected from the group consisting of peliomycin (NSC 76455),

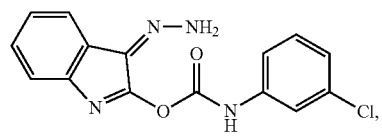

NSC 320852

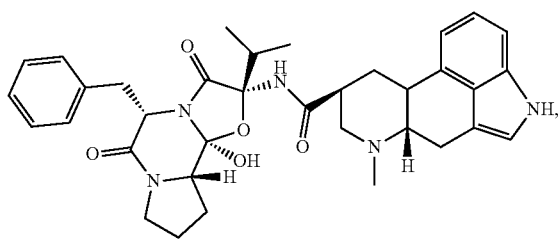

NSC 409663

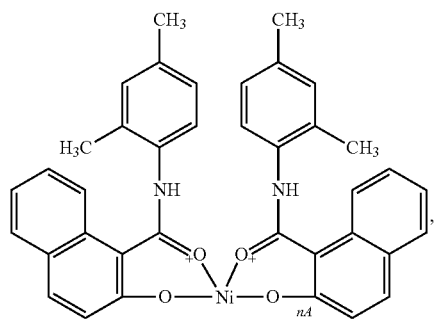

NSC 306698

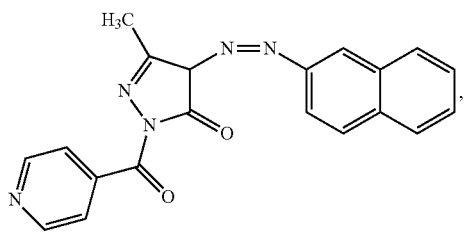

NSC 303769

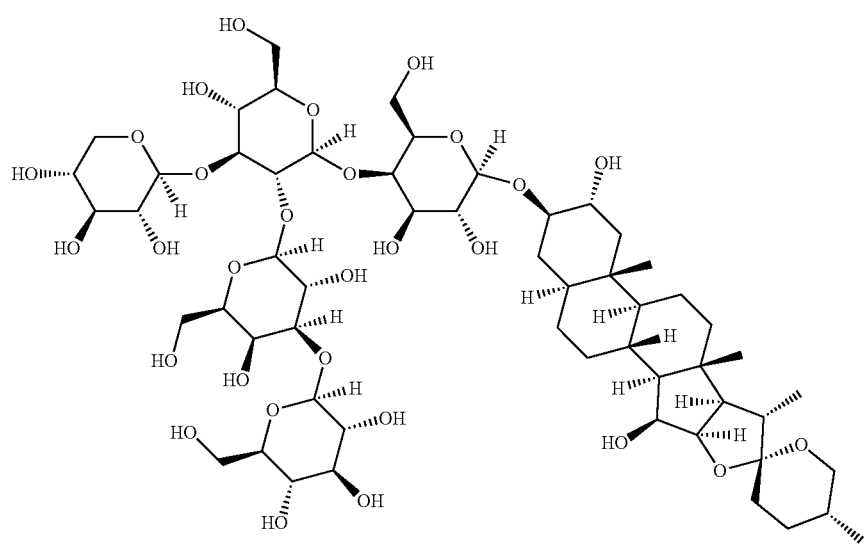

NSC 23471

NSC 11668

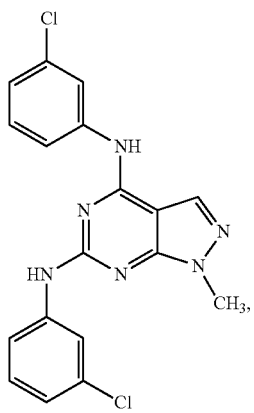

NSC 19139

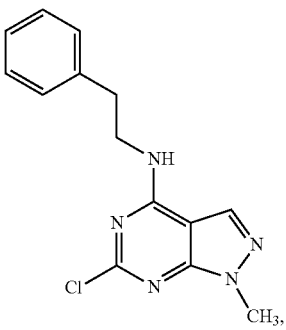

NSC 375985

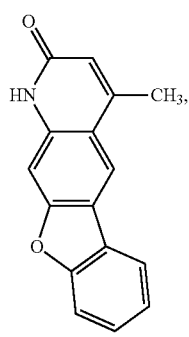

NSC 120688

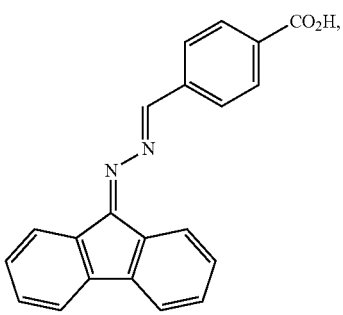

NSC 168201

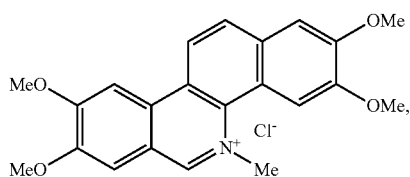

and any combination thereof, wherein A of NSC306698 is a mono- or divalent anion and n=1 or 2 depending on the valency of A. A can be any suitable mono- or divalent anion (e.g., a Group VII anion, such as Br⁻, Cl⁻, or I⁻).

By "enhancing the chemotherapeutic treatment" is meant that the chemotherapeutic agent has a greater effect (e.g., at least a 5% increase, at least a 10% increase, at least a 20% increase, at least a 30% increase, at least a 40% increase, at least a 50% increase, at least a 60% increase, at least a 70% increase, at least an 80% increase, etc.) in the presence of at least one compound described herein than in the absence of that compound. Since ABCG2 is a mediator of resistance, if a compound described herein inhibits ABCG2, the cancerous cell is less resistant to the chemotherapeutic agent, thereby making it more susceptible to the cytotoxicity of the agent.

The present invention also provides a method of reducing resistance of a cancer cell to a chemotherapeutic agent by inhibiting ABCG2 in a mammal, which method comprises administering to the mammal an effective amount of a compound selected from the group consisting of peliomycin (NSC 76455),

NSC 320852

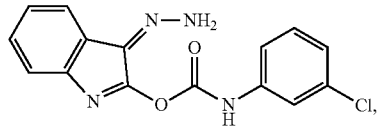

NSC 409663

-continued
NSC 306698
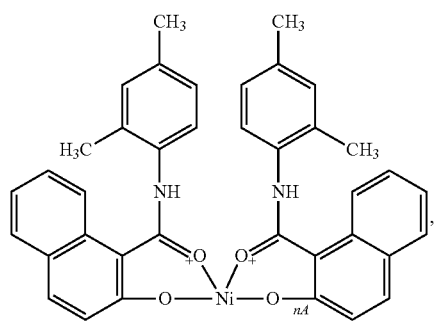
NSC 303769
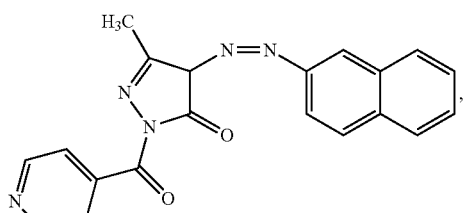
NSC 23471
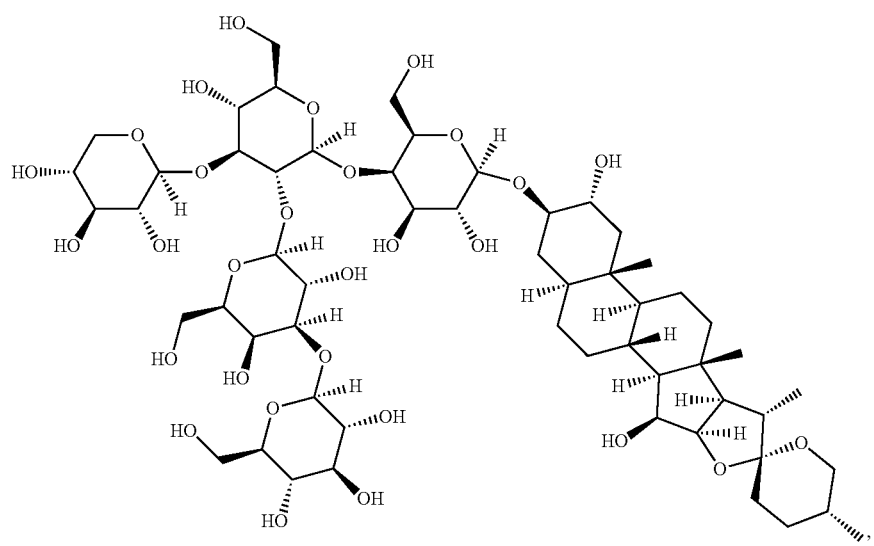
NSC 11668
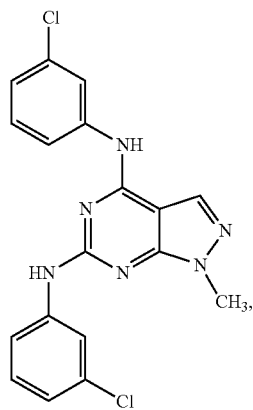
NSC 19139
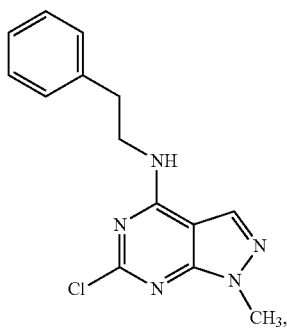
NSC 375985
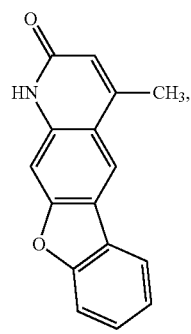
NSC 120688
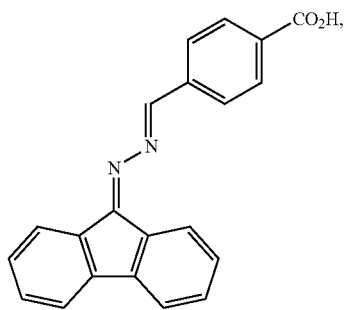

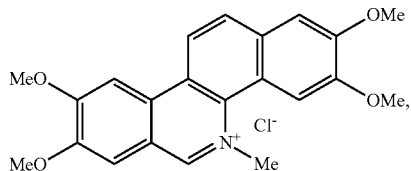

NSC 168201 and any combination thereof, wherein A of NSC306698 is a mono- or divalent anion and n=1 or 2 depending on the valency of A, whereupon resistance of the chemotherapeutic agent is reduced in the mammal. By "reducing resistance of a chemotherapeutic agent" is meant that cancer cells that are treated by the chemotherapeutic agent have resistance reversed, development of resistance is reduced, or a combination thereof. For example, resistance is reduced by at least 5%, at least 10%, at least 20%, at least 30%, at least 40%, at least 50%, at least 60%, at least 70%, or at least 80%.

The chemotherapeutic agent described herein can be any cytotoxic drug that is useful to kill cancer cells. In embodiments, the agent is any drug in which there is resistance to a cancer cell upon administration. For example, the agent can be an antimetabolite (e.g., methotrexate), a mitotic inhibitor (e.g., docetaxel, paclitaxel, vinblastine), an alkylating agent (e.g., cisplatin), a cytotoxic antibiotic (e.g., daunorubicin, doxorubicin, mitoxantrone), a topoisomerase inhibitor (e.g., topotecan, irinotecan, camptothecin, SN-38), a tyrosine kinase inhibitor (e.g., gefitinib), or any combination thereof. Specific examples of the chemotherapeutic agent include mitoxantrone, topotecan, irinotecan, flavopiridol, gefitinib, methotrexate, rhodamine, daunomycin, imatinib, doxorubicin, colchincine, vinblastine, paclitaxel, cisplatin, adriamycin, danofloxacin mesylate, and/or docetaxel.

In some embodiments, the chemotherapeutic agent is mitoxantrone, topotecan, irinotecan, flavopiridol, gefitinib, methotrexate, or any combination thereof.

Any method known in the art can be used to measure the enhancement of the chemotherapeutic agent and/or the reduction of resistance. The Examples section describes exemplary methods. Alternatively, cells can be contacted with a toxic chemotherapy drug, such as mitoxantrone or topotecan, in an amount that permits cell survival due to the resistance conferred by ABCG2. Cell viability can be measured by a colorimetric assay (Skehan et al., *J. Natl. Cancer Inst.* 82: 1107 1112 (1990)), by counting cells with a cell counter, or by incorporation of tritiated thymidine.

The cells are then contacted with a compound of the invention that inhibits ABCG2. The enhancement of the chemotherapeutic agent and/or reduction of resistance can then be detected by measuring the growth inhibition of cells, using a variety of means, such as $IC_{50}$ measurements, vital staining, metabolite measurements, or confocal microscopy. Confocal microscopy can be used to determine whether a particular drug has been retained or accumulated in the cell.

The invention further provides a method of inhibiting ABCG2 in a mammal afflicted with cancer, which method comprises administering to the mammal an effective amount of a compound selected from the group consisting of peliomycin (NSC 76455),

NSC 320852

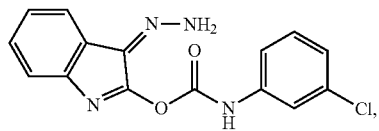

NSC 409663

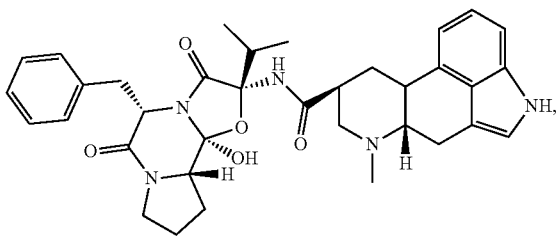

NSC 306698

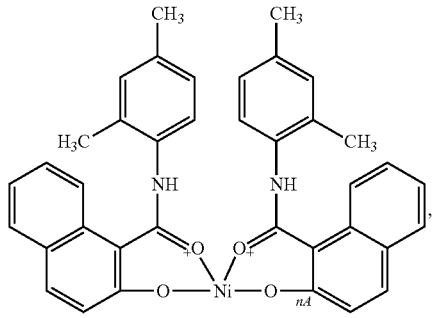

NSC 303769

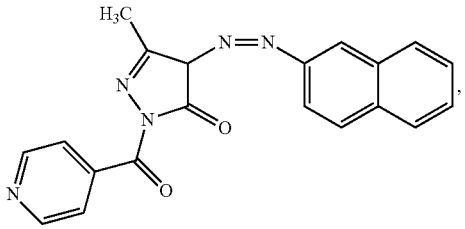

-continued

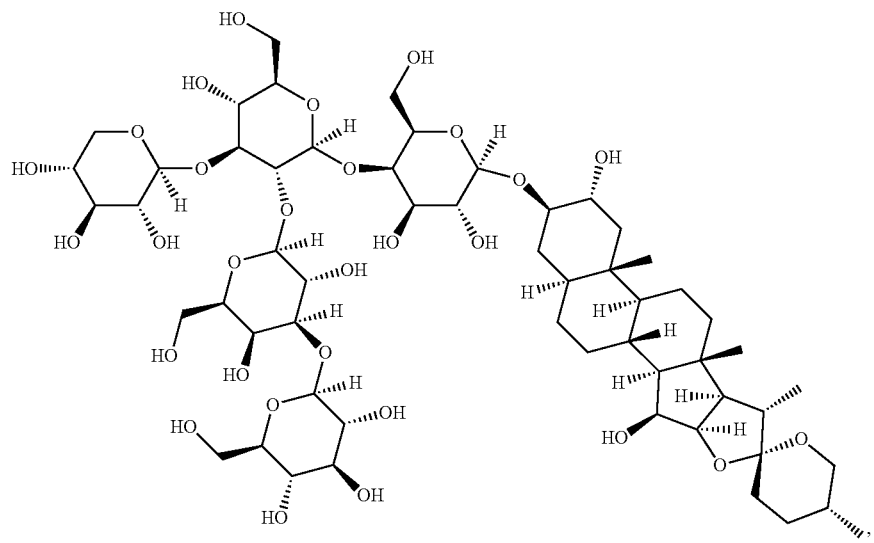

NSC 11668

NSC 23471

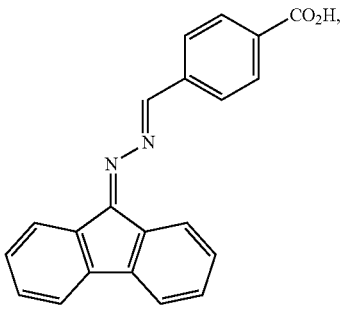

NSC 19139

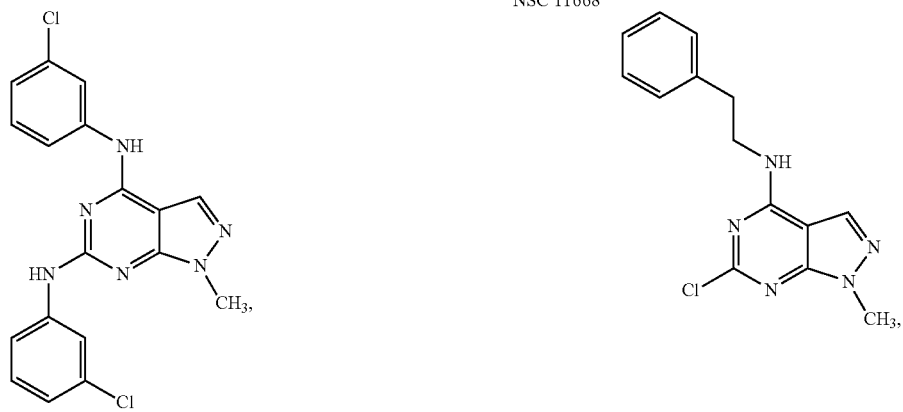

NSC 375985

NSC 120688

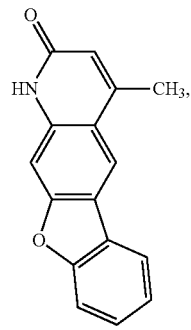

NSC 168201

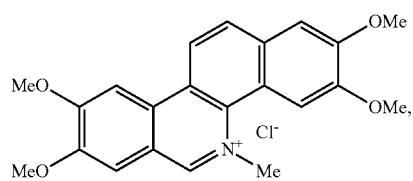

and any combination thereof, wherein A of NSC306698 is a mono- or divalent anion and n=1 or 2 depending on the valency of A, whereupon ABCG2 is inhibited in the mammal.

Since ABCG2 has also been reported to be expressed at high levels in the digestive tract and at the blood-brain barrier (Takano et al., *Pharmacol. Ther.*, 109: 137-61 (2006)), it is envisioned that ABCG2 inhibitors can enhance bioavailability (e.g., oral bioavailability) and brain penetration of ABCG2 substrate drugs, such as, e.g., topotecan. Thus, in an embodiment, the present invention provides a method of increasing the bioavailability of an ABCG2 substrate drug in a mammal, which method comprises administering to the mammal an effective amount of the ABCG2 substrate drug in conjunction with an effective amount of a compound to inhibit ABCG2 protein, said compound being selected from the group consisting of peliomycin (NSC 76455),
NSC 320852
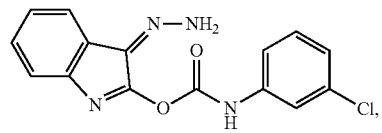
NSC 409663
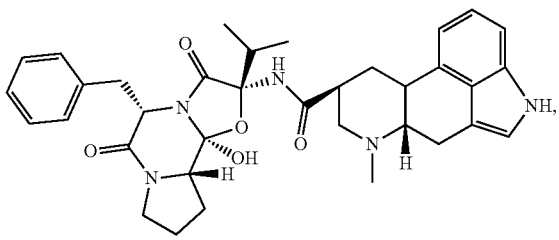
NSC 306698
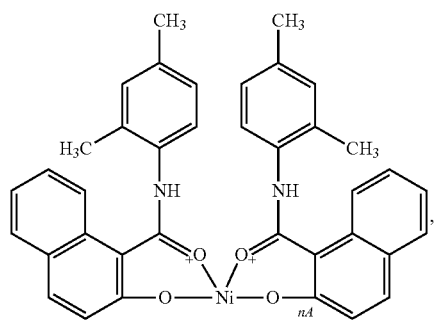
NSC 303769
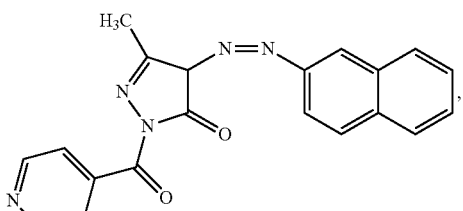
NSC 23471
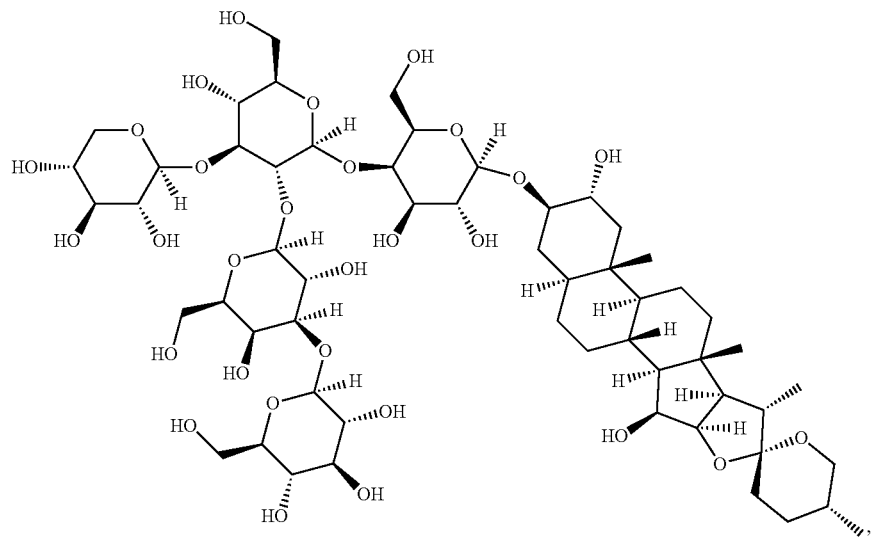
NSC 11668
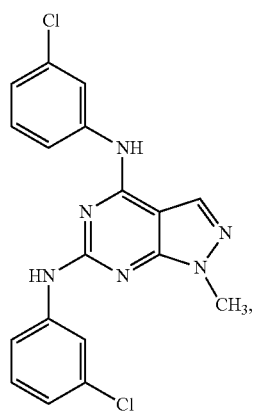
NSC 19139
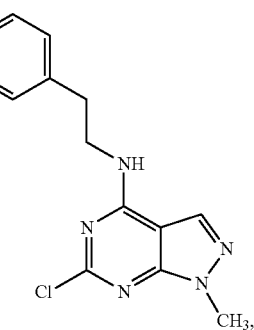

-continued

NSC 375985

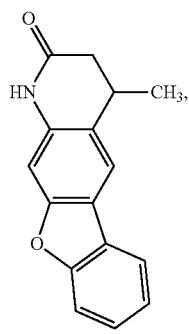

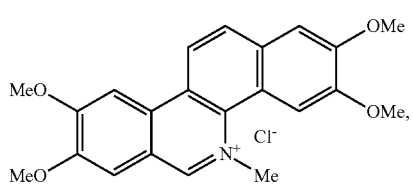

NSC 120688

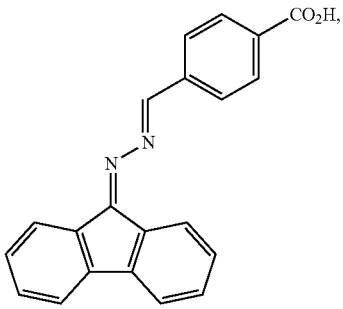

NSC 168201

NSC 11668

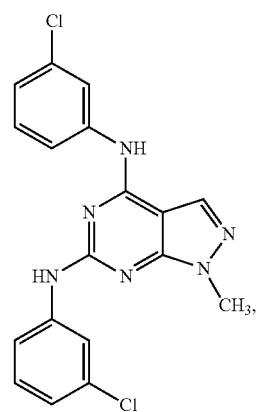

NSC 19139

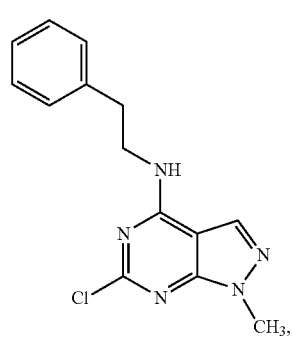

and any combination thereof, wherein A of NSC306698 is a mono- or divalent anion and n=1 or 2 depending on the valency of A. Since CNS penetration can be enhanced by administration of a compound of the invention, such method is useful in the treatment of cancer, such as brain tumors, CNS metastases, and/or gastrointestinal stromal tumors.

The ABCG2 substrate drug can be, for example, an antimetabolite (e.g., methotrexate), a mitotic inhibitor (e.g., docetaxel, paclitaxel, vinblastine), an alkylating agent (e.g., cisplatin), a cytotoxic antibiotic (e.g., daunorubicin, doxorubicin, mitoxantrone), a topoisomerase inhibitor (e.g., topotecan, irinotecan, camptothecin, SN-38), a tyrosine kinase inhibitor (e.g., gefitinib), or any combination thereof. Specific examples of the ABCG2 substrate drug include mitoxantrone, topotecan, irinotecan, flavopiridol, gefitinib, methotrexate, rhodamine, daunomycin, imatinib, doxorubicin, colchincine, vinblastine, paclitaxel, cisplatin, adriamycin, danofloxacin mesylate, docetaxel, or any combination thereof. In some embodiments, the ABCG2 substrate drug is mitoxantrone, topotecan, irinotecan, flavopiridol, gefitinib, and/or methotrexate.

Pgp, MRP1, and ABCG2 are the major contributors to multidrug resistance in most cancer cells in culture (Szakacs et al., *Nat. Rev. Drug Discov.*, 5: 219-34 (2006)). ABCG2 has overlapping substrate specificity with MRP1 and Pgp. Accordingly, in an embodiment, the present invention provides a method of inhibiting MRP1 in a mammal afflicted with cancer, which method comprises administering to the mammal an effective amount of a compound selected from the group consisting of

NSC 375985

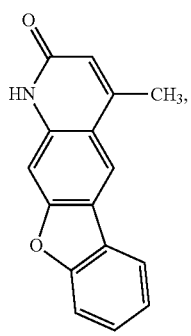

NSC 120688

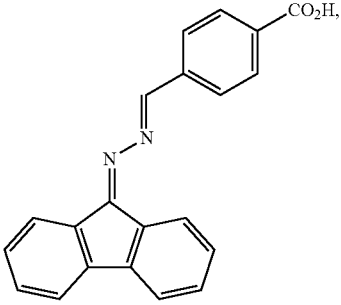

and any combination thereof, whereupon MRP1 is inhibited in the mammal.

In preferred embodiments of the methods described herein, the compound is selected from the group consisting of

NSC 11668

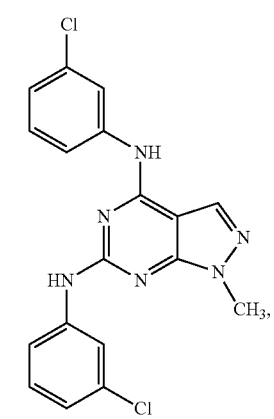

NSC 168201

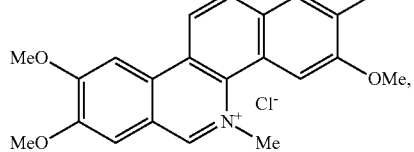

and any combination thereof.

All of the methods described herein have applicability to the treatment of any type of cancer that over-expresses ABCG2 (and/or MRP1) and is capable of being treated with a chemotherapeutic agent. Such cancers include, for example, leukemias (e.g., acute myeloid leukemia (AML), chronic myeloid leukemia (CML)), solid tumors (e.g., of the lung, endometrium, or digestive tract), melanomas, non-small cell lung cancer tumors, colon tumors, prostate tumors, brain tumors, lymphomas, breast tumors, ovarian tumors, lung tumors, and stomach tumors.

NSC 19139

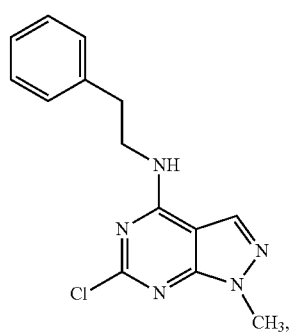

For purposes of the present inventive methods, the mammal includes, without limitation, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

NSC 375985

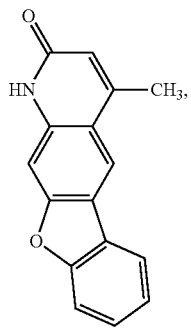

The methods of the present invention encompass administration of a pharmaceutical composition comprising (i) a compound selected from the group consisting of peliomycin (NSC 76455),

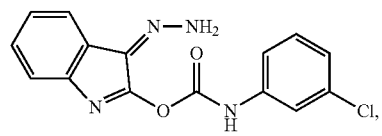
NSC 320852
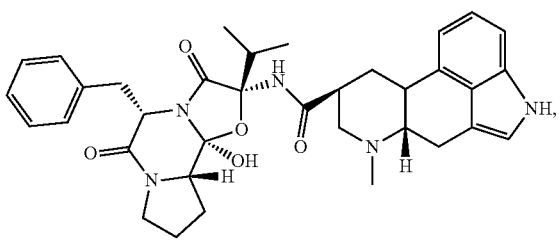
NSC 306698
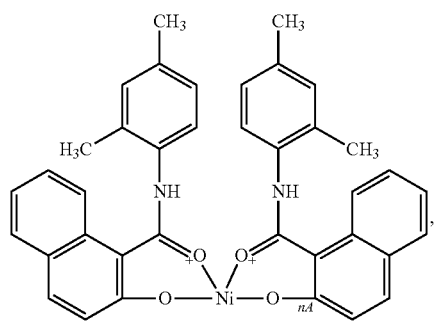
NSC 409663
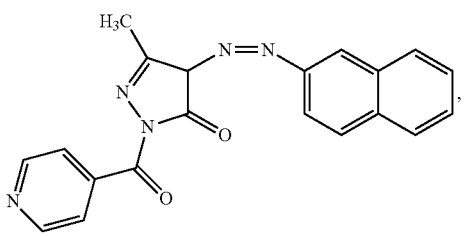
NSC 303769
NSC 23471
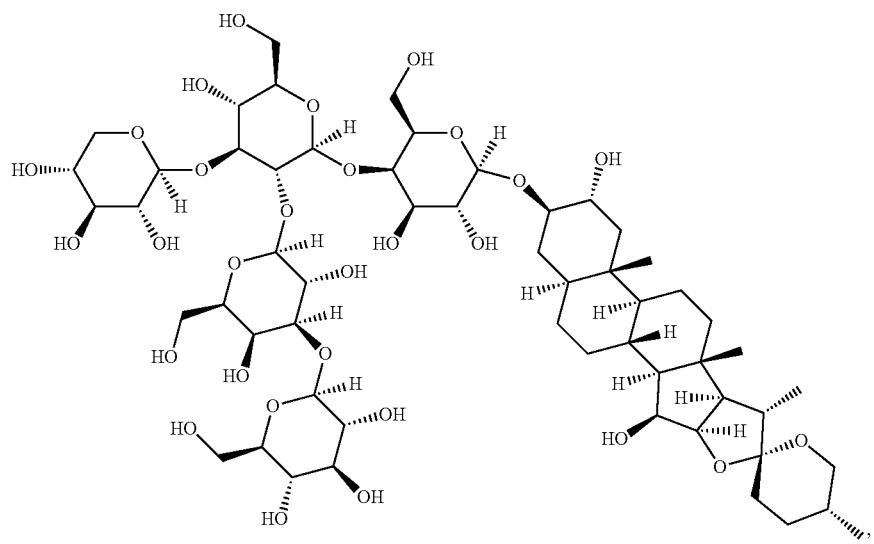
NSC 11668
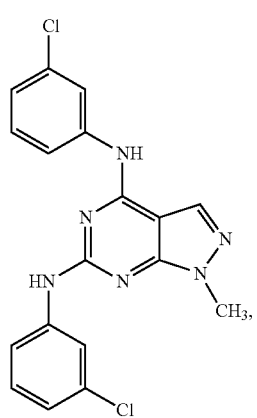
NSC 19139
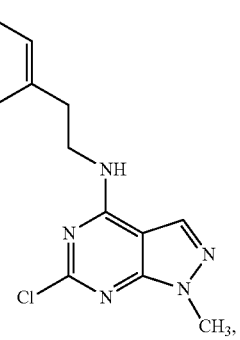

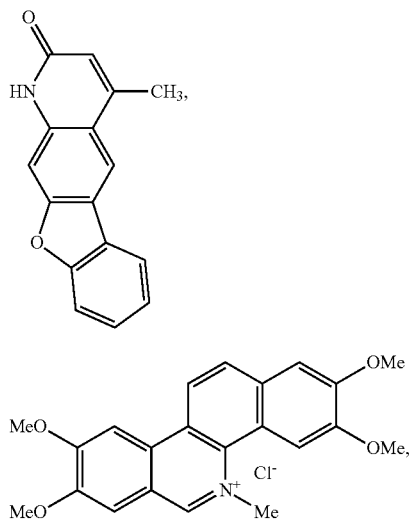

NSC 375985

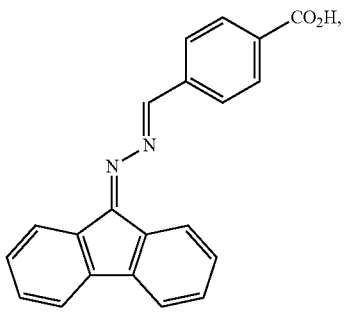

NSC 120688

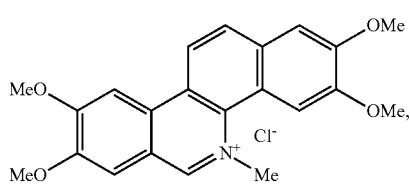

NSC 168201 and any combination thereof, wherein A of NSC306698 is a mono- or divalent anion and n=1 or 2 depending on the valency of A and (ii) a pharmaceutically acceptable carrier.

Generally, the compounds of the invention will be administered in a pharmaceutical composition to an individual afflicted with a cancer. Those undergoing or about to undergo chemotherapy can be treated with at least one compound described herein separately or in conjunction with other treatments, as appropriate. In therapeutic applications, compositions are administered to a patient in an amount sufficient to elicit an effective depression of ABCG2 activity thereby potentiating the cytotoxicity of the chemotherapeutic treatment. A dose adequate to accomplish this is defined as an "effective amount," which is also an "ABCG2 inhibiting effective amount." Amounts effective for a therapeutic or prophylactic use will depend on, e.g., the stage and severity of the disease being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. It will be appreciated by one of skill in the art that various disease states may require prolonged treatment involving multiple administrations, perhaps using a series of different ABCG2 inhibitors and/or chemotherapeutic agents in each or various rounds of administration.

Suitable chemotherapeutic agents administered in coordination with at least one compound of the present invention include mitoxantrone, topotecan, irinotecan, flavopiridol, gefitinib, methotrexate, rhodamine, daunomycin, imatinib, doxorubicin, colchincine, vinblastine, paclitaxel, cisplatin, adriamycin, danofloxacin mesylate, camptothecin, SN-38, and/or docetaxel. The chemotherapeutic agent is administered in a dose sufficient to treat the cancer (e.g., cancer-treatment effective amount of a chemotherapeutic agent). Such doses are known in the art (see, for example, the *Physicians' Desk Reference* (2004)). Such agents can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present inventive methods can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response, e.g., as determined by measuring cancer-specific antigens or other measurable parameters related to the tumor load of a patient.

Any of the compound of the invention is administered in a dose sufficient to enhance the effect of the chemotherapeutic agent and/or reduce drug resistance in a cancer. A suitable dosage is that which will result in a concentration of the compound of the invention in the cancerous cells to be treated sufficient to inhibit ABCG2 activity, e.g., from about 10 nM to 200 nM intracellularly, which can require an extracellular concentration of from about 10 µM to 50 µM. The dose can be adjusted as necessary to enhance the effect of the chemotherapeutic agent and/or reduce drug resistance.

The pharmaceutical compositions for therapeutic treatment are intended for any suitable mode of administration, including parenteral, topical, oral, or local administration and generally comprise a pharmaceutically acceptable carrier and an amount of the active ingredient sufficient to reduce, and preferably prevent, the activity of ABCG2. The carrier can be any of those conventionally used and is limited only by chemico-physical considerations, such as solubility and lack of reactivity with the compound of the invention, and by the route of administration.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Preferably a compound of the invention and a chemotherapeutic agent are coadministered to the mammal. By "coadministering" is meant administering the chemotherapeutic agent and a compound of the invention sufficiently close in time such that a compound of the invention can enhance the effect of the chemotherapeutic agent. In this regard, a compound of the invention can be administered first and the chemotherapeutic agent can be administered second, or vice versa. Alternatively, a compound of the invention and the chemotherapeutic agent can be administered simultaneously. In addition, a combination of compounds of the invention can be administered, and one or more of the compounds of the invention can be administered in combination with another agent useful in the treatment of cancer.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, a compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The concentration of a compound of the present invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, a compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The following examples further illustrate the invention but, of course, should not be construed as in any way limiting its scope.

EXAMPLES

Pheophorbide a (PhA) is obtained from Frontier Scientific (Logan, Utah). Fumetrimorgin C (FTC), libraries of pure natural products, and synthetic molecules (structural diversity and mechanistic diversity sets) and individual compounds are from the Drug Synthesis and Chemistry Branch, Developmental Therapeutics Program (DTP), Division of Cancer Treatment and Diagnostics, National Cancer Institute (Bethesda, Md.). Cell culture media are from Invitrogen (Carlsbad, Calif.), fetal bovine serum (FBS) from Hyclone (Kansas City, Mo.), and phosphate-buffered saline (PBS) from Quality Biological (Gaithersburg, Md.).

Intracellular fluorescence of BODIPY-prazosin, rhodamine 123, or calcein fluorescence is detected with a FACSort flow cytometer equipped with a 488 nm argon laser and 530 nm bandpass filter. APC fluorescence is measured with a 635 nm read diode laser and 561 nm longpass filter. At least 10000 events are collected. Dead cells are eliminated based on propidium iodide exclusion.

Apparent $IC_{50}$ values are calculated from dose-response data using SigmaPlot (SPSS, Inc., Chicago) 4-parameter logistic nonlinear regression analysis. Unless otherwise noted, all data are presented as average±sem.

Example 1

This example demonstrates a screening assay for ABCG2 inhibitors in accordance with an embodiment of the invention.

To prepare the cell culture, NCI-H460 human lung non-small-cell carcinoma cells (National Cancer Institute, Frederick, Md.) are selected for over-expression of ABCG2 by maintenance in RPMI1640/10% FBS supplemented with 20 nM mitoxantrone (Robey et al., *Biochim. Biophys. Acta*, 1512: 171-82 (2001)). After removal of mitoxantrone, cells are further grown in the same medium without mitoxantrone for 5-30 days. These cells are designated NCI-H460/MX20. Parental cells (low ABCG2 expression) (Robey et al., vide supra) are maintained in the same medium without mitoxantrone. ABCG2-transfected or MDR1-transfected (i.e. Pgp-expressing) HEK293 cells are maintained in 2 mg/ml G418 as previously described (Robey et al., *Br. J. Cancer*, 89: 1971-8 (2003)). MRP1-transfected HEK293 cells are maintained in 5 µM etoposide. MCF-7 FLV1000 cells are maintained in Richter's medium with 10% FCS and Pen/strep with 1000 nM flavopiridol (Robey et al., *Clin. Cancer Res.*, 7: 145-52 (2001)).

Accumulation of pheophorbide a, a fluorescent ABCG2 substrate (Jonker et al., *Proc. Natl. Acad. Sci. USA*, 99: 15649-54 (2002) and Robey et al., *Cancer Res.*, 64: 1242-6 (2004)), formed the basis of the assay for inhibitors of ABCG2 activity (Henrich et al., *J. Biomol. Screen*, 11: 176-83 (2006)). Briefly, NCI-H460/MX20 cells are transferred to black wall, clear bottom 384-well polylysine-coated assay plates (Corning, Corning, N.Y.) and allowed to attach for several hours. Pheophorbide a (1 µM final concentration) is added immediately followed by compounds or vehicle (DMSO/PBS) control and incubated an additional 18 h. After removal of medium and washing with PBS containing $Ca^{2+}$ and $Mg^{2+}$, fluorescence intensity is read on a Tecan Safire fluorescence plate reader in bottom read mode, 395 nm excitation, 670 nm emission. Each plate has control wells containing 10 μM (final concentration) FTC. Data are normalized to FTC and reported as % of FTC fluorescence.

FIG. 1 summarizes the activities of the compounds in accordance with an embodiment of the invention in the pheophorbide a accumulation assay. The compounds have activities ranging from 60-105% of the activity of FTC when evaluated at 10 μM. In this assay, $IC_{50}$ for FTC was 0.8 μM (Henrich et al., 2006, vide supra). The data also are summarized in Table 1 below.

Example 2

This example demonstrates an assay to determine the ability of compounds to sensitize cancer cells to killing by mitoxantrone in accordance with an embodiment of the invention.

The ability of compounds to sensitize NCI-H460/MX20 cells to killing by mitoxantrone is assessed as described in Henrich et al. (*J. Biomol. Screen*, 11: 176-83 (2006)). ABCG2 over-expressing cells or parental cells are treated with mitoxantrone in the presence or absence of 10 μM compound (or 1 μM FTC) and cell numbers assessed after 2 d by an XTT assay (Scudiero et al., *Cancer Res.*, 48: 4827-33 (1988)). Final DMSO concentration is 0.2% (v/v).

Figure 2:
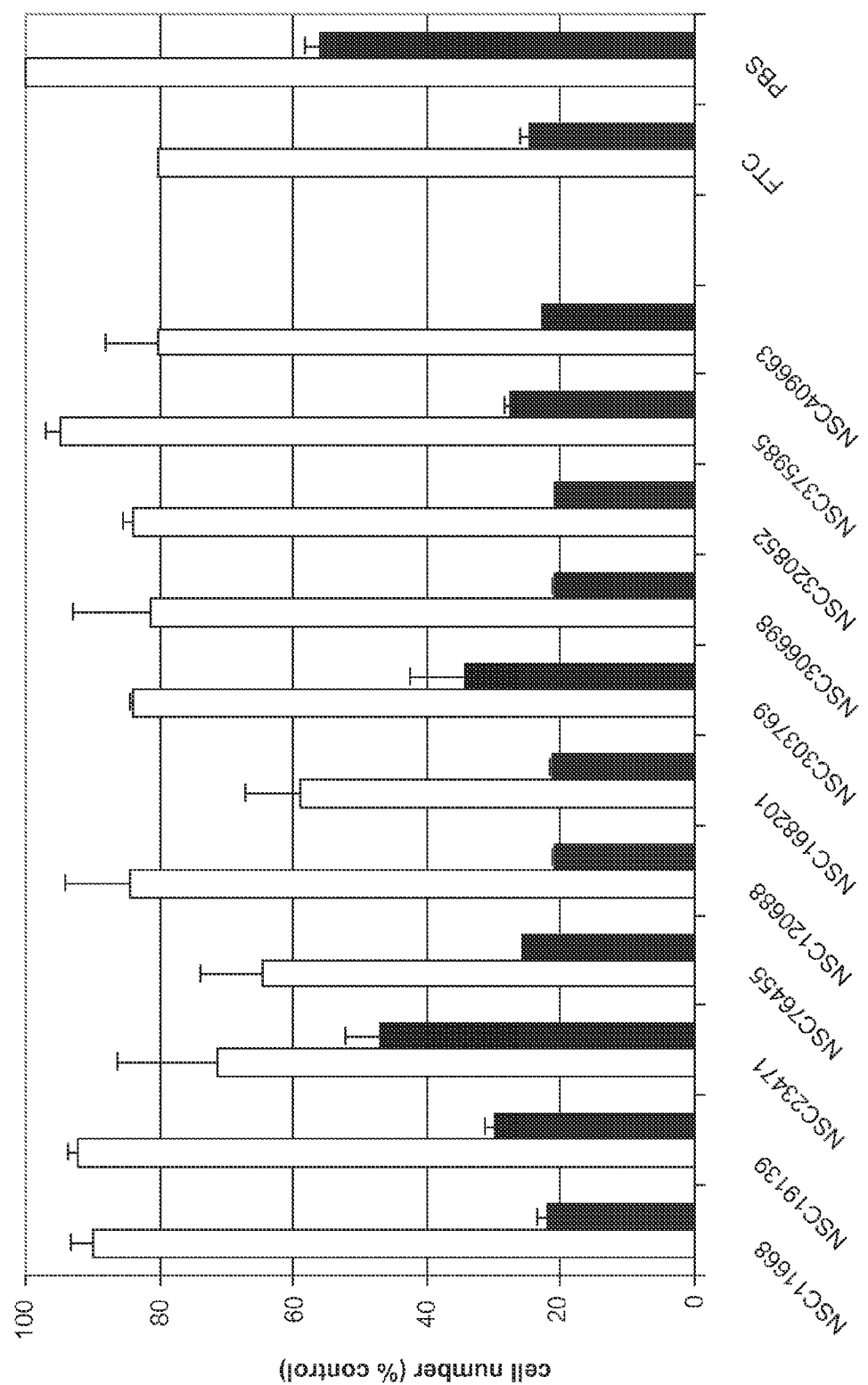
FIG. 2 depicts the sensitization of ABCG2-overexpressing cells to mitoxantrone in an embodiment of the invention. Cell survival is normalized to buffer control (no mitoxantrone, no compound=100%). Error bars represent range of duplicate determinations. The white bars indicate mitoxantrone administration alone, whereas the gray bars indicate administration of 30 μM mitoxantrone and a compound of the invention.

FIG. 2 illustrates each compound's ability to restore mitoxantrone sensitivity to cells overexpressing ABCG2. Unselected NCI-H460 cells are sensitive to killing by mitoxantrone. After 2 days in the presence of 30 μM mitoxantrone, cell numbers are 21.6±1.6% (sd) of control (vehicle). None of the compounds tested are significantly cytotoxic against parental cells (data not shown). Cells selected for ABCG2 overexpression (NCI-H460/MX20) are significantly more resistant to mitoxantrone (see "PBS" column in FIG. 2). After mitoxantrone treatment, NCI-H460/MX20 cell number is 56.1±2.1% (sd) of control. In the presence of 1 μM FTC, this number is further reduced to 24.5±1.5% (sd). Similar effects are seen with other tested compounds (at 10 μM). None of the compounds alone causes significant cell killing in the NCI-H460/MX20 subline (FIG. 2). The data also are summarized in Table 1 below.

Example 3

This example demonstrates that compounds in accordance with an embodiment of the invention can inhibit ABCG2-mediated transport using BODIPY-prazosin as a substrate (Robey et al., *Br. J. Cancer*, 89: 1971-8 (2003)). This example also demonstrates that exemplary compounds inhibit MRP1-mediated calcein efflux (Robey et al., 2003, vide supra and Alvarez et al., *Mol. Pharmacol.*, 54: 802-14 (1998)).

Transfected HEK293 cells expressing ABCG2, Pgp, or MRP1 are trypsinized and incubated in complete medium (phenol red-free Richter's medium with 10% FCS and penicillin/streptomycin) containing 200 nM BODIPY-prazosin, 0.5 μg/ml rhodamine 123 or 200 nM calcein AM, respectively, in the presence or absence of the desired concentration of inhibitor for 30 min at 37° C. The positive controls for inhibition of ABC transporters are 10 μM FTC for ABCG2, 3 μg/ml valspodar for Pgp and 25 μM MK-571 for MRP1. Cells are then washed and incubated in substrate-free medium continuing with or without inhibitor for 1 h.

Figure 3A:
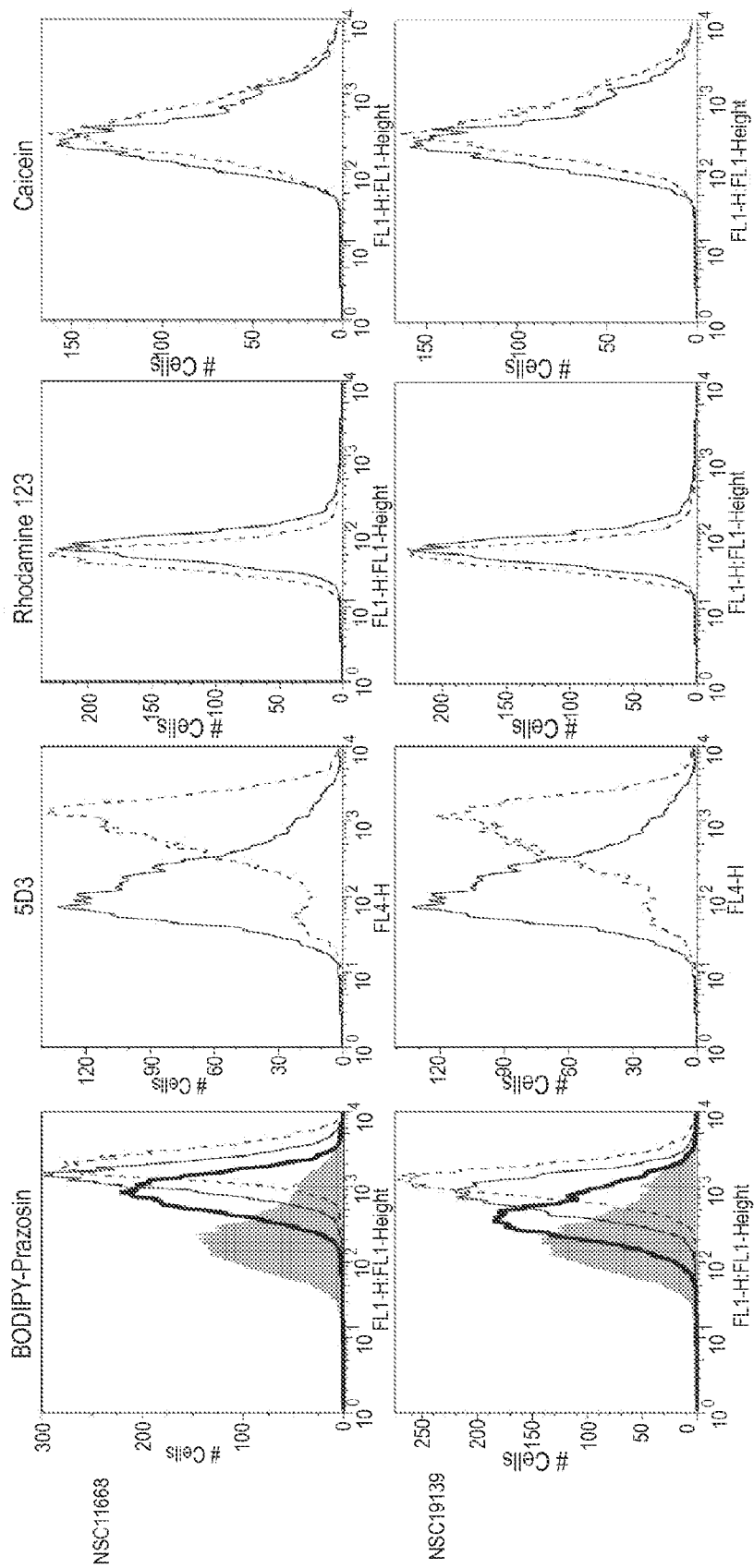
FIGS. 3A-3C depict functional assays of the effects of compounds on ABCG2 and MRP1 in an embodiment of the invention. Column 1 in FIG. 3A-3C: ABCG2 transfected cells are incubated in BODIPY-prazosin in the absence (shaded histogram) or presence of 0.1 (heavy solid line), 1 (solid line), or 10 μM (dashed line) of NSC11668, NSC19139, NSC120688, NSC168201 or NSC375985. FTC (10 μM, bottom histogram) is shown as a positive control for ABCG2 inhibition. Column 2 in FIG. 3A-3C: ABCG2 transfected cells are incubated with unlabeled 5D3 antibody (1:3500) in the absence (solid line) or presence (dashed line) of 20 μM of a compound after which cells are incubated in APC-labeled secondary antibody. FTC (bottom histogram) at a concentration of 20 μM is shown as a positive control. Column 3 in FIG. 3A-3C: MDR1-transfected cells are incubated in 0.5 μg/ml rhodamine 123 in the absence (solid line) or presence (dashed line) of 10 μM of the desired inhibitor. Valspodar at 3 μg/ml is included as a positive control for Pgp inhibition (bottom histogram). Column 4 in FIG. 3A-3C: MRP1-transfected cells are incubated in 200 nM calcein AM in the absence (solid line) or presence (dashed line) of 10 μm of the compounds. MK-571 (25 μM) is shown (bottom histogram) as a positive control for inhibition of MRP1 transport.
Figure 3B:
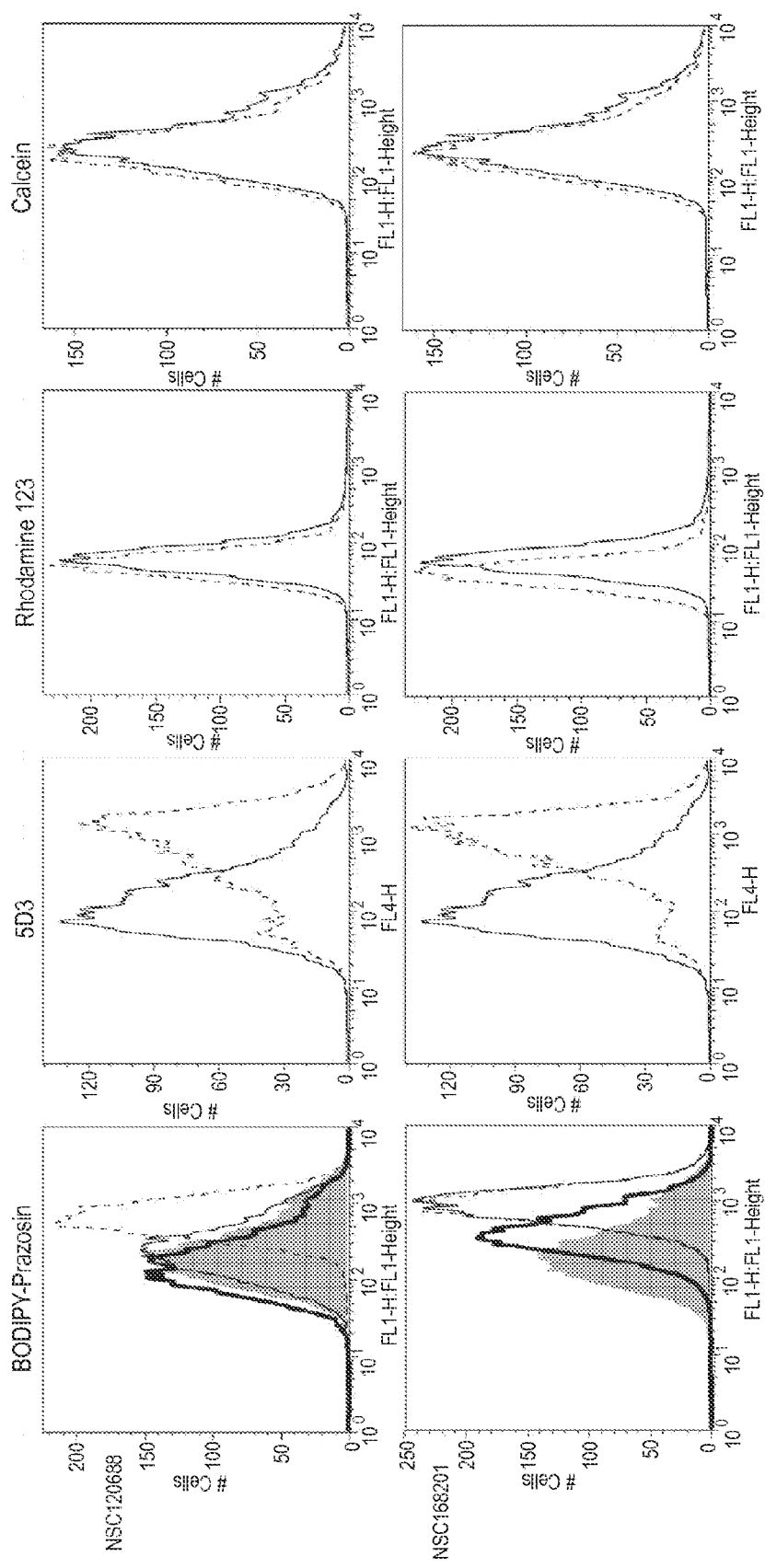
Figure 3C:
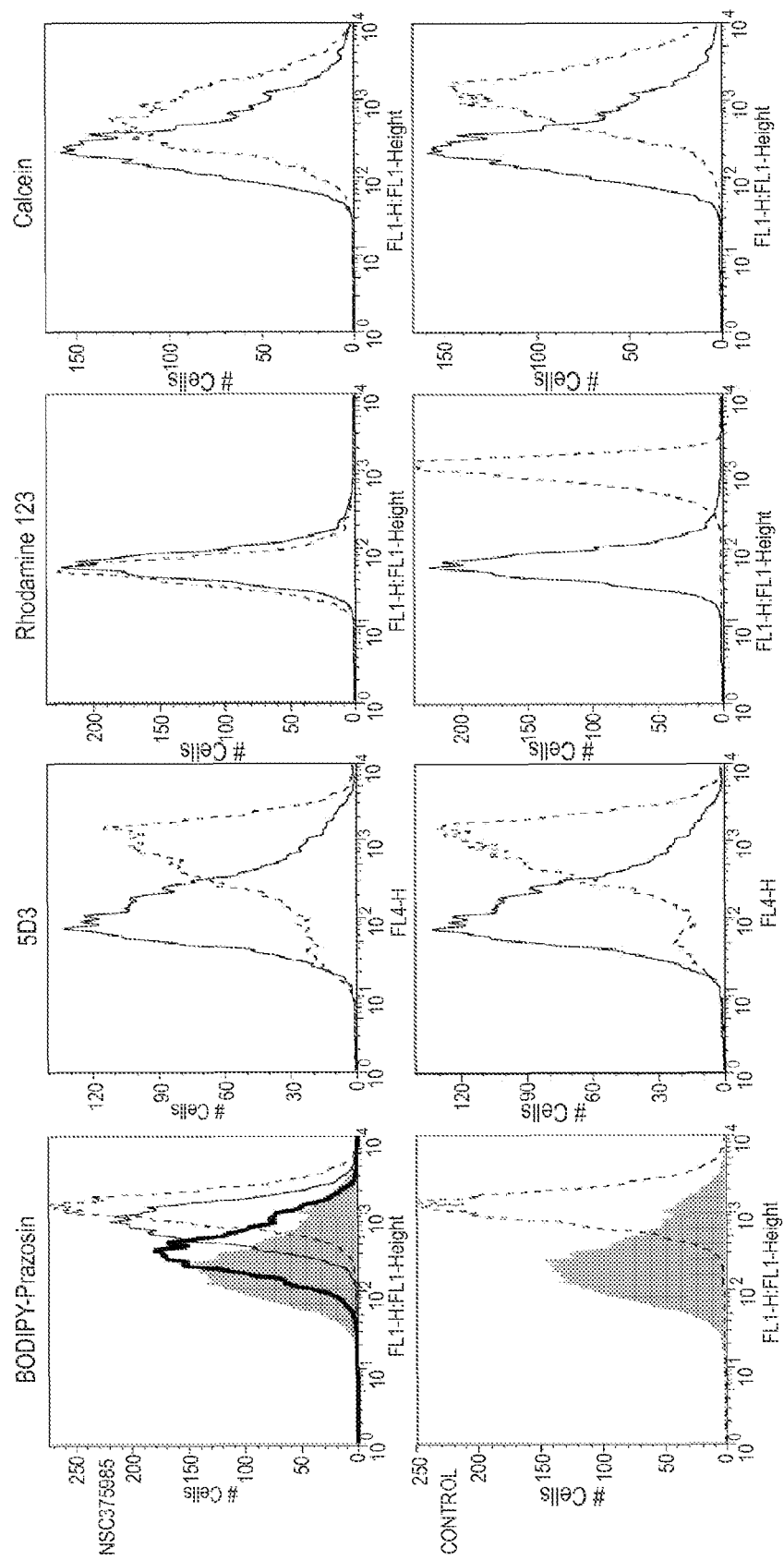

In this assay, compounds of the invention are active in inhibiting BODIPY-prazosin efflux (1.4- to 5.9-fold BODIPY-prazosin accumulation as compared to 3.5-fold for FTC). Compounds: NSC11668, NSC19139, NSC120688, NSC168201, and NSC375985 are selected for further testing. Column 1 of FIG. 3 shows the results of a dose-response assay with BODIPY-prazosin with 0.1, 1, or 10 μM of each of the 5 compounds. The data also are summarized in Table 1 below.

Example 4

This example demonstrates that compounds of the invention are ABCG2 inhibitors, rather than substrates, in accordance with an embodiment of the invention.

Five compounds are examined for their ability to increase surface staining of the 5D3 antibody. Ozvegy-Laczka et al. have previously demonstrated that, at high dilution, the 5D3 antibody binds more readily to ABCG2 when ABCG2-transfected cells are incubated with the antibody in the presence of an ABCG2 inhibitor (*J. Biol. Chem.*, 280: 4219-27 (2005)). This is believed to be due to the fact that, at low antibody concentrations, 5D3 has a higher affinity for a certain conformation induced by inhibitors of ABCG2, allowing study by flow cytometry.

The 5D3 shift assay is performed as described by Ozvegy-Laczka et al. with minor modifications. ABCG2-transfected HEK293 cells are trypsinized and incubated with 5D3 antibody (1:3500, eBioscience, San Diego, Calif.) for 2 h in the presence or absence of 20 μM of each of the compounds or 20 μM FTC as a positive control. Cells are subsequently washed and incubated with APC-labeled goat anti-mouse secondary antibody (1:35) for 30 min after which the cells are washed and analyzed. FIG. 3, column 2 shows that, at 20 μM, all of the compounds tested increase 5D3 binding and are comparable to 20 μM FTC shown as a positive control. The change in APC fluorescence is quantified for each sample, and the values are given in Table 1.

TABLE 1

Summary of effects of compounds in multiple assays

| Compound | Pheophorbide a | | MX sensitization[b] | Flow-ABCG2 | | IAAP binding[e] | Cross-reactivity (flow) | |
|---|---|---|---|---|---|---|---|---|
| | total[a] | $IC_{50}$ (μM) | | 5D3[c] | BODIPY-prazosin[d] | | Pgp[f] | MRP1[g] |
| NSC11668 | 84.1 | 4.5 | 21.9 | 4.0 | 5.9 | 24.6 | 0.73 | 1.2 |
| NSC19139 | 76.6 | 2.6 | 30.0 | 3.6 | 3.5 | 33.5 | 0.77 | 1.3 |
| NSC120688 | 67.2 | 4.3 | 20.9 | 3.7 | 2.0 | 19.1 | 0.84 | 0.81 |
| NSC168201 | 104.5 | 3.9 | 21.2 | 3.7 | 2.6 | 34.2 | 0.64 | 0.81 |
| NSC375985 | 63.8 | 3.7 | 27.6 | 3.2 | 3.6 | 48.7 | 0.84 | 1.8 |
| FTC (control) | 100 | 0.8 | 24.5 | 3.7 | 3.5 | 32.7 | | |

TABLE 1-continued

Summary of effects of compounds in multiple assays

| | Pheophorbide a | | | Flow-ABCG2 | | | Cross-reactivity (flow) | |
|---|---|---|---|---|---|---|---|---|
| Compound | total[a] | IC$_{50}$ (μM) | MX sensitization[b] | 5D3[c] | BODIPY-prazosin[d] | IAAP binding[e] | Pgp[f] | MRP1[g] |
| MK571 (25 μM) (control) | | | | | | | | 3.3 |
| valspodar (3 μg/mL) (control) | | | | | | | 14.9 | |
| DMSO/PBS (blank) | 0 | | 56.1 | 1.0 | 1.0 | 100 | | |

[a] % of FTC response
[b] % NCI-H460/MX20 cell survival in the presence of compound and mitoxantrone
[c] 5D3 staining: treated/control ratio at 10 μM compound
[d] BODIPY-prazosin efflux: treated/control ratio at 10 μM compound
[e] Blocking of $^{125}$I-IAAP binding: % of control binding in the presence of 20 μM compound
[f] Pgp inhibition, rhodamine efflux: treated/control ratio at 10 μM compound
[g] MRP1 inhibition, calcein efflux: treated/control ratio at 10 μM compound Example 5

This example demonstrates photoaffinity labeling of ABCG2 with [$^{125}$I]-IAAP. Specifically, the example demonstrates the ability of compounds in accordance with an embodiment of the invention to inhibit [$^{125}$I]IAAP incorporation into ABCG2 in membranes isolated from ABCG2-overexpressing MCF-7 FLV1000 cells.

ABCG2 expressed in MCF-7 FLV1000 cells is photolabeled with [$^{125}$I]-IAAP as described previously (Shukla et al., Biochemistry, 45: 8940-51 (2006)). Briefly, crude membranes (1 mg protein/me of MCF-7 FLV1000 cells are incubated with 20 μM of the indicated compound for 10 min at room temperature in 50 mM Tris-HCl, pH 7.5. 3-6 nM [$^{125}$I]-IAAP (2200 Ci/mmole) (PerkinElmer Life Sciences, Wellesley, Mass.) is added, and the samples are incubated for an additional 5 min under subdued light. The samples are then exposed to ultraviolet (UV, 365 nm) light for 10 min, and the labeled ABCG2 is immunoprecipitated using BXP-21 antibody. The radioactivity incorporated into the ABCG2 band is quantified using the STORM 860 PhosphorImager system (Molecular Dynamics, Sunnyvale, Calif.) and ImageQuaNT software (Molecular Dynamics).

Since IAAP is a photoaffinity analog of prazosin, it is thought to label the drug binding site. All 5 compounds tested (at 20 μM) significantly reduce [$^{125}$I]-IAAP incorporation into ABCG2 (FIG. 4). It is believed that the decreased binding is due to competition of the test compounds for the drug binding site.

Example 6

This Example demonstrates that an ABGC2 inhibitor enhances the chemotherapeutic treatment of a camptothecin derivative SN-38 in accordance with an embodiment of the invention.

Cytotoxicity assays were performed based on the sulforhodamine B assay reported by Skehan et al (JNCI 1990). Cells were plated at a density of 10,000 cells/well in 96-well plates and allowed to attach overnight at 37° C. in 5% CO$_2$. The ABGC2 inhibitor compounds were subsequently added at various concentrations and plates were allowed to incubate for 96 h at 37° C. in 5% CO$_2$. Cells were then fixed with 50% trichloroacetic acid, washed and allowed to dry.

Plates were then stained with sulforhodamine B solution (0.4% sulforhodamine B w/v in 1% acetic acid) for 30 minutes and washed 3 times in 1% acetic acid solution. Sulforhodamine was then solubilized with 10 mM Tris Base and optical densities were ready on a plate reader at an absorbance of 570 nm. Each concentration was tested in quadruplicate and controls were performed in replicates of eight.

The ABCG2 inhibitor compounds were used at 1 μM with varying doses of SN-38, FTC at 5 μM is the positive control for inhibition. The results are shown in FIGS. 5A-5F. The IC50 values decrease when the ABCG2 transfected cells are exposed to the ABCG2 inhibitor and treated with SN-38. The foregoing shows that the ABCG2 inhibitor enhances the chemotherapeutic treatment of a cancer treatment agent.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of enhancing the chemotherapeutic treatment of tumor or cancer with a chemotherapeutic agent or a method of increasing the bioavailability of an ABCG2 substrate drug in a mammal, which method comprises administering to the mammal an effective amount of the chemotherapeutic agent in conjunction with an effective amount of a compound to inhibit ABCG2 protein, said compound being selected from the group consisting of:

NSC 11668

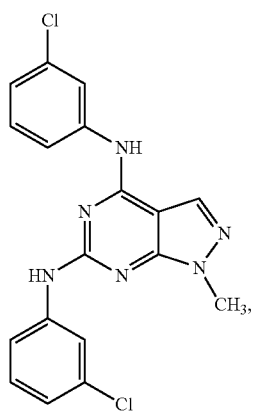

NSC 19139

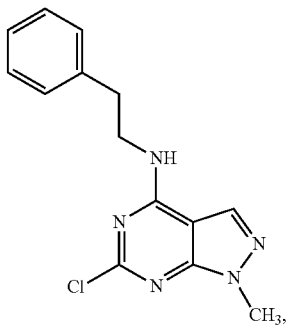

NSC 375985

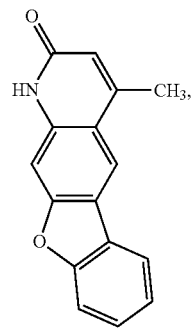

NSC 120688

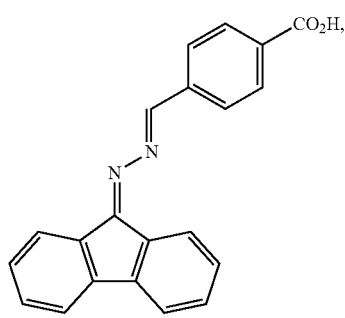

and any combination thereof,
wherein the tumor or cancer is selected from those of solid tumor, melanoma, non-small cell lung cancer, colon tumor, prostate tumor, brain tumor, lymphoma, breast tumor, ovarian tumor, lung tumor, and stomach tumor; and
wherein the chemotherapeutic agent is selected from the group consisting of mitoxantrone, topotecan, camptothecin, camptothecin derivative SN-38, irinotecan, flavopiridol, gefitinib, rhodamine, daunomycin, imatinib, doxorubicin, colchincine, vinblastine, paclitaxel, cisplatin, adriamycin, danofloxacin mesylate, docetaxel, and a combination thereof.

2. The method of claim 1, wherein the tumor is selected from prostate tumor, brain tumor, lymphoma, ovarian tumor, and stomach tumor.

3. The method of claim 2, wherein the tumor is selected from prostate tumor, brain tumor, lymphoma, and stomach tumor.

4. A method of reducing resistance of a tumor or cancer to a chemotherapeutic agent by inhibiting ABCG2 in a mammal, which method comprises administering to the mammal, in conjunction with the administration of the chemotherapeutic agent, an effective amount of a compound selected from the group consisting of:

NSC 11668

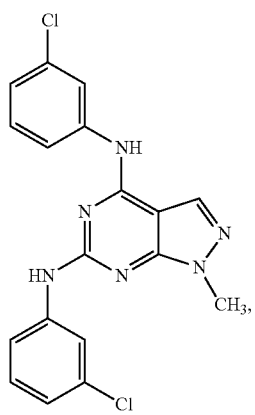

NSC 19139

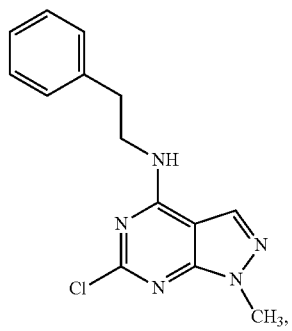

NSC 375985

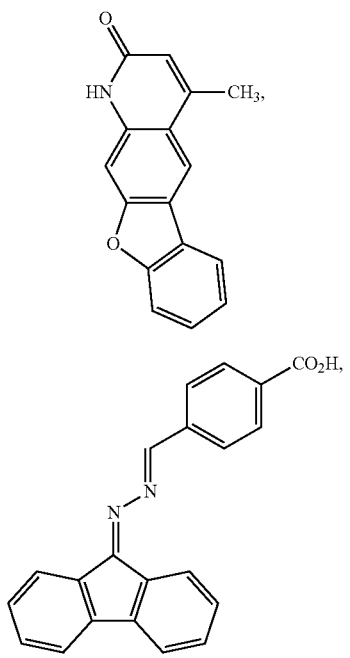

NSC 120688 vopiridol, gefitinib, rhodamine, daunomycin, imatinib, doxorubicin, colchincine, vinblastine, paclitaxel, cisplatin, adriamycin, danofloxacin mesylate, docetaxel, and a combination thereof.

5. The method of claim 4, wherein the tumor is selected from prostate tumor, brain tumor, lymphoma, ovarian tumor, and stomach tumor.

6. The method of claim 5, wherein the tumor is selected from prostate tumor, brain tumor, lymphoma, and stomach tumor.

7. A method of reducing resistance of a tumor or cancer to a chemotherapeutic agent by inhibiting MRP1 in a mammal, which method comprises administering to the mammal, in conjunction with the administration of the chemotherapeutic agent, an effective amount of a compound selected from the group consisting of

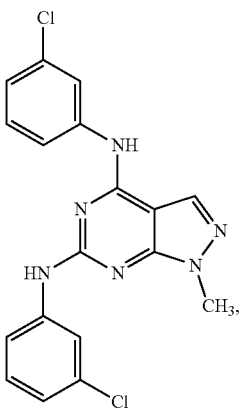

NSC 11668

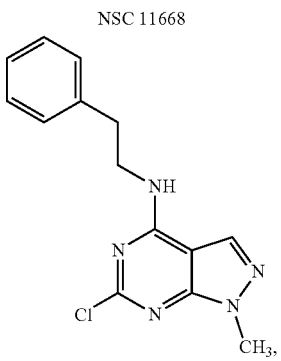

NSC 19139

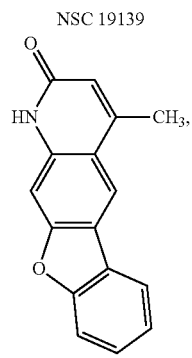

NSC 375985 and any combination thereof, whereupon resistance of the chemotherapeutic agent is reduced in the mammal, wherein the tumor or cancer is selected from those of solid tumor, melanoma, non-small cell lung cancer, colon tumor, prostate tumor, brain tumor, lymphoma, breast tumor, ovarian tumor, lung tumor, and stomach tumor; and wherein the chemotherapeutic agent is selected from the group consisting of mitoxantrone, topotecan, camptothecin, camptothecin derivative SN-38, irinotecan, flaand any combination thereof, whereupon MRP1 is inhibited in the mammal and whereupon resistance of the chemotherapeutic agent is reduced in the mammal, wherein the tumor or cancer is selected from those of solid tumor, melanoma, non-small cell lung cancer, colon tumor, prostate tumor, brain tumor, lymphoma, breast tumor, ovarian tumor, lung tumor, and stomach tumor; and wherein the chemotherapeutic agent is selected from the group consisting of mitoxantrone, topotecan, camptothecin, camptothecin derivative SN-38, irinotecan, flavopiridol, gefitinib, rhodamine, daunomycin, imatinib, doxorubicin, colchincine, vinblastine, paclitaxel, cisplatin, adriamycin, danofloxacin mesylate, docetaxel, and a combination thereof.

8. The method of claim 7, wherein the tumor is selected from prostate tumor, brain tumor, lymphoma, ovarian tumor, and stomach tumor.

9. The method of claim 8, wherein the tumor is selected from prostate tumor, brain tumor, lymphoma, and stomach tumor.

\* \* \* \* \*